US012734331B2

(12) United States Patent
Howell et al.

(10) Patent No.: US 12,734,331 B2
(45) Date of Patent: Sep. 15, 2026

(54) COMPACT INSERTION ASSEMBLIES OF RAPIDLY INSERTABLE CENTRAL CATHETERS AND METHODS THEREOF

(71) Applicant: Bard Access Systems, Inc., Salt Lake City, UT (US)

(72) Inventors: Glade H. Howell, Draper, UT (US); Daniel B. Blanchard, Bountiful, UT (US); Jason R. Stats, Layton, UT (US); Kyle G. Thornley, Farmington, UT (US); Joe Spataro, Cottonwood Heights, UT (US); Eric W. Lindekugel, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1002 days.

(21) Appl. No.: 17/953,663

(22) Filed: Sep. 27, 2022

(65) Prior Publication Data

US 2023/0101455 A1 Mar. 30, 2023

Related U.S. Application Data

(60) Provisional application No. 63/271,043, filed on Oct. 22, 2021, provisional application No. 63/249,009, filed on Sep. 27, 2021.

(51) Int. Cl.

*A61M 25/01* (2006.01)
*A61M 25/00* (2006.01)

(52) U.S. Cl.

CPC ........ *A61M 25/01* (2013.01); *A61M 25/0097* (2013.01); *A61M 25/0026* (2013.01)

(58) Field of Classification Search

CPC .......... A61M 25/0097; A61M 25/0606; A61M 25/09041; A61M 2025/0177;

(Continued)

(56) References Cited

U.S. PATENT DOCUMENTS

| | | | |
|---|---|---|---|
| 1,013,691 | A | 1/1912 | Shields |
| 3,225,762 | A | 12/1965 | Guttman |

(Continued)

FOREIGN PATENT DOCUMENTS

| | | | |
|---|---|---|---|
| DE | 202012006191 | U1 | 7/2012 |
| EP | 0653220 | A1 | 5/1995 |

(Continued)

OTHER PUBLICATIONS

PCT/US2021/057135 filed Oct. 28, 2021 International Preliminary Report on Patentability dated May 2, 2023.

(Continued)

*Primary Examiner* — Kami A Bosworth
(74) *Attorney, Agent, or Firm* — Rutan & Tucker LLP

(57) ABSTRACT

Disclosed are compact rapidly insertable central catheter ("RICC") insertion assemblies and methods. For example, a RICC insertion assembly can include a RICC, an introducer assembly, an access guidewire, and a coupler coupling together the RICC and the introducer assembly. The RICC can include a catheter tube, a catheter hub, and one or more extension legs connected in the foregoing order. The introducer assembly can include an introducer needle coupled to a syringe. The introducer needle can include a needle-hub through hole passing through a needle hub and connecting to a needle-shaft lumen of a needle shaft. The access guidewire can include a proximal portion disposed in the RICC and a distal portion disposed in the needle-shaft lumen through the needle-hub through hole. The coupler can enforce a loop in the access guidewire over which the catheter tube follows, thereby compacting the RICC insertion assembly and making it easier to handle.

13 Claims, 27 Drawing Sheets

(58) Field of Classification Search
CPC .... A61M 2025/018; A61M 2025/0681; A61M 2025/09125
See application file for complete search history.

(56) References Cited

U.S. PATENT DOCUMENTS 3,325,061 A 6/1967 Ellsworth
3,382,872 A 5/1968 Rubin
3,570,485 A 3/1971 Reilly
3,890,976 A 6/1975 Bazell et al.
3,991,762 A 11/1976 Radford
4,205,675 A 6/1980 Vaillancourt
4,292,970 A 10/1981 Hession, Jr.
4,445,893 A 5/1984 Bodicky
4,468,224 A 8/1984 Enzmann et al.
4,484,915 A 11/1984 Tartaglia
4,525,157 A 6/1985 Vaillancourt
4,581,019 A 4/1986 Curelaru et al.
4,582,181 A * 4/1986 Samson .............. A61M 25/104 604/95.01
4,594,073 A 6/1986 Stine
4,639,248 A 1/1987 Schweblin
4,702,735 A 10/1987 Luther et al.
4,743,265 A 5/1988 Whitehouse et al.
4,766,908 A 8/1988 Clement
4,863,432 A 9/1989 Kvalo
4,935,008 A 6/1990 Lewis, Jr.
4,950,252 A 8/1990 Luther et al.
4,957,489 A 9/1990 Cameron et al.
4,994,040 A 2/1991 Cameron et al.
5,017,259 A 5/1991 Kohsai
5,040,548 A 8/1991 Yock
5,057,073 A 10/1991 Martin
5,112,312 A 5/1992 Luther
5,115,816 A 5/1992 Lee
5,120,317 A 6/1992 Luther
5,158,544 A 10/1992 Weinstein
5,167,634 A 12/1992 Corrigan, Jr. et al.
5,188,593 A 2/1993 Martin
5,195,962 A * 3/1993 Martin ................ A61M 25/003 604/43
5,207,650 A 5/1993 Martin
RE34,416 E 10/1993 Lemieux
5,267,958 A 12/1993 Buchbinder et al.
5,290,241 A 3/1994 Kraus et al.
5,292,309 A 3/1994 Van Tassel et al.
5,295,970 A 3/1994 Clinton et al.
5,306,247 A 4/1994 Pfenninger
5,312,361 A 5/1994 Zadini et al.
5,322,512 A 6/1994 Mohiuddin
5,328,472 A 7/1994 Steinke et al.
5,350,358 A 9/1994 Martin
5,358,495 A 10/1994 Lynn
5,364,355 A 11/1994 Alden et al.
5,368,567 A 11/1994 Lee
5,378,230 A 1/1995 Mahurkar
5,380,290 A 1/1995 Makower et al.
5,389,087 A 2/1995 Miraki
5,439,449 A 8/1995 Mapes et al.
5,443,457 A 8/1995 Ginn et al.
5,460,185 A 10/1995 Johnson et al.
5,489,271 A 2/1996 Andersen
5,573,520 A 11/1996 Schwartz et al.
5,584,813 A 12/1996 Livingston et al.
5,662,622 A 9/1997 Gore et al.
5,683,370 A 11/1997 Luther et al.
5,713,876 A 2/1998 Bogert et al.
5,718,678 A 2/1998 Fleming, III
5,772,636 A 6/1998 Brimhall et al.
5,885,251 A 3/1999 Luther
5,919,164 A 7/1999 Andersen
5,921,971 A 7/1999 Agro et al.
5,947,940 A 9/1999 Beisel
5,951,518 A 9/1999 Licata et al.
5,957,893 A 9/1999 Luther et al.
5,971,957 A 10/1999 Luther et al.
6,159,198 A 12/2000 Gardeski et al.
6,197,007 B1 3/2001 Thorne et al.
6,206,849 B1 3/2001 Martin et al.
6,228,062 B1 5/2001 Howell et al.
6,273,874 B1 8/2001 Parris
6,475,187 B1 11/2002 Gerberding
6,533,782 B2 3/2003 Howell et al.
6,551,284 B1 4/2003 Greenberg et al.
6,606,515 B1 8/2003 Windheuser et al.
6,616,630 B1 9/2003 Woehr et al.
6,626,868 B1 9/2003 Prestidge et al.
6,626,869 B1 9/2003 Bint
6,638,252 B2 10/2003 Moulton et al.
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,991,625 B1 1/2006 Gately et al.
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,094,222 B1 8/2006 Siekas et al.
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 5/2008 Katoh et al.
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 4/2010 Brimhall
7,722,567 B2 5/2010 Tal
D617,893 S 6/2010 Bierman et al.
D624,643 S 9/2010 Bierman et al.
7,819,889 B2 10/2010 Healy et al.
7,857,788 B2 12/2010 Racz
D630,729 S 1/2011 Bierman et al.
7,909,797 B2 3/2011 Kennedy, II et al.
7,909,811 B2 3/2011 Agro et al.
7,922,696 B2 4/2011 Tal et al.
7,938,820 B2 5/2011 Webster et al.
7,967,834 B2 6/2011 Tal et al.
7,976,511 B2 7/2011 Fojtik
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,361,011 B2 1/2013 Mendels
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 2/2014 Tal et al.
8,672,888 B2 3/2014 Tal
8,696,645 B2 4/2014 Tal et al.
8,784,362 B2 7/2014 Boutilette et al.
8,827,958 B2 9/2014 Bierman et al.
8,876,704 B2 11/2014 Golden et al.
8,882,713 B1 11/2014 Call et al.
8,900,192 B2 12/2014 Anderson et al.
8,900,207 B2 12/2014 Uretsky
8,915,884 B2 12/2014 Tal et al.
8,956,327 B2 2/2015 Bierman et al.
9,023,093 B2 5/2015 Pal
9,067,023 B2 6/2015 Bertocci
9,126,012 B2 9/2015 McKinnon et al.
9,138,252 B2 9/2015 Bierman et al.
9,180,275 B2 11/2015 Helm
9,265,920 B2 2/2016 Rundquist et al.

(56) References Cited

U.S. PATENT DOCUMENTS

| | | | |
|---|---|---|---|
| 9,272,121 | B2 | 3/2016 | Piccagli |
| 9,445,734 | B2 | 9/2016 | Grunwald |
| 9,522,254 | B2 | 12/2016 | Belson |
| 9,554,785 | B2 | 1/2017 | Walters et al. |
| 9,566,087 | B2 | 2/2017 | Bierman et al. |
| 9,675,784 | B2 | 6/2017 | Belson |
| 9,713,695 | B2 | 7/2017 | Bunch et al. |
| 9,764,117 | B2 | 9/2017 | Bierman et al. |
| 9,770,573 | B2 | 9/2017 | Golden et al. |
| 9,814,861 | B2 | 11/2017 | Boutillette et al. |
| 9,820,845 | B2 | 11/2017 | von Lehe et al. |
| 9,861,383 | B2 | 1/2018 | Clark |
| 9,872,971 | B2 | 1/2018 | Blanchard |
| 9,884,169 | B2 | 2/2018 | Bierman et al. |
| 9,889,275 | B2 | 2/2018 | Voss et al. |
| 9,913,585 | B2 | 3/2018 | McCaffrey et al. |
| 9,913,962 | B2 | 3/2018 | Tal et al. |
| 9,981,113 | B2 | 5/2018 | Bierman |
| 10,010,312 | B2 | 7/2018 | Tegels |
| 10,065,020 | B2 | 9/2018 | Gaur |
| 10,086,170 | B2 | 10/2018 | Chhikara et al. |
| 10,098,724 | B2 | 10/2018 | Adams et al. |
| 10,111,683 | B2 | 10/2018 | Tsamir et al. |
| 10,118,020 | B2 | 11/2018 | Avneri et al. |
| 10,130,269 | B2 | 11/2018 | McCaffrey et al. |
| 10,220,184 | B2 | 3/2019 | Clark |
| 10,220,191 | B2 | 3/2019 | Belson et al. |
| 10,265,508 | B2 | 4/2019 | Baid |
| 10,271,873 | B2 | 4/2019 | Steingisser et al. |
| 10,376,675 | B2 | 8/2019 | Mitchell et al. |
| 10,675,440 | B2 | 6/2020 | Abitabilo et al. |
| 10,688,281 | B2 | 6/2020 | Blanchard et al. |
| 10,806,901 | B2 | 10/2020 | Burkholz et al. |
| 10,926,060 | B2 | 2/2021 | Stern et al. |
| 11,260,206 | B2 | 3/2022 | Stone et al. |
| 11,400,260 | B2 | 8/2022 | Huang et al. |
| 11,759,607 | B1 | 9/2023 | Biancarelli |
| 2002/0040231 | A1 | 4/2002 | Wysoki |
| 2002/0045843 | A1 | 4/2002 | Barker et al. |
| 2002/0123755 | A1 | 9/2002 | Lowe et al. |
| 2002/0198492 | A1 | 12/2002 | Miller et al. |
| 2003/0036712 | A1 | 2/2003 | Heh et al. |
| 2003/0060863 | A1 | 3/2003 | Dobak |
| 2003/0088212 | A1 | 5/2003 | Tal |
| 2003/0100849 | A1 | 5/2003 | Jang |
| 2003/0153874 | A1 | 8/2003 | Tal |
| 2003/0158514 | A1 | 8/2003 | Tal |
| 2004/0015138 | A1 | 1/2004 | Currier et al. |
| 2004/0049157 | A1 | 3/2004 | Plishka et al. |
| 2004/0064086 | A1 | 4/2004 | Gottlieb et al. |
| 2004/0092879 | A1 | 5/2004 | Kraus et al. |
| 2004/0116864 | A1 | 6/2004 | Boudreaux |
| 2004/0116901 | A1 | 6/2004 | Appling |
| 2004/0167478 | A1 | 8/2004 | Mooney et al. |
| 2004/0193093 | A1 | 9/2004 | Desmond |
| 2004/0230178 | A1 | 11/2004 | Wu |
| 2005/0004554 | A1 | 1/2005 | Osborne |
| 2005/0120523 | A1 | 6/2005 | Schweikert |
| 2005/0131343 | A1 | 6/2005 | Abrams et al. |
| 2005/0148936 | A1 | 7/2005 | Moss |
| 2005/0215956 | A1 | 9/2005 | Nerney |
| 2005/0215958 | A1 | 9/2005 | Hawthorne |
| 2005/0245882 | A1 | 11/2005 | Elkins et al. |
| 2005/0283221 | A1 | 12/2005 | Mann et al. |
| 2006/0009740 | A1 | 1/2006 | Higgins et al. |
| 2006/0116629 | A1 | 6/2006 | Tal et al. |
| 2006/0129100 | A1 | 6/2006 | Tal |
| 2006/0129130 | A1 | 6/2006 | Tal et al. |
| 2006/0135973 | A1 | 6/2006 | Hawkins et al. |
| 2007/0276288 | A1 | 11/2007 | Khaw |
| 2008/0045894 | A1 | 2/2008 | Perchik et al. |
| 2008/0091137 | A1 | 4/2008 | Reavill |
| 2008/0125744 | A1 | 5/2008 | Treacy |
| 2008/0125748 | A1 | 5/2008 | Patel |
| 2008/0132850 | A1 | 6/2008 | Fumiyama et al. |
| 2008/0262430 | A1 | 10/2008 | Anderson et al. |
| 2008/0262431 | A1 | 10/2008 | Anderson et al. |
| 2008/0294111 | A1 | 11/2008 | Tal et al. |
| 2008/0312578 | A1 | 12/2008 | DeFonzo et al. |
| 2008/0319387 | A1 | 12/2008 | Amisar et al. |
| 2009/0131872 | A1 | 5/2009 | Popov |
| 2009/0187147 | A1 | 7/2009 | Kurth et al. |
| 2009/0221961 | A1 | 9/2009 | Tal et al. |
| 2009/0270889 | A1 | 10/2009 | Tal et al. |
| 2009/0292272 | A1 | 11/2009 | McKinnon |
| 2010/0030154 | A1 | 2/2010 | Duffy |
| 2010/0256487 | A1 | 10/2010 | Hawkins et al. |
| 2010/0298839 | A1 | 11/2010 | Castro |
| 2010/0305474 | A1 | 12/2010 | DeMars et al. |
| 2011/0004162 | A1 | 1/2011 | Tal |
| 2011/0009827 | A1 | 1/2011 | Bierman et al. |
| 2011/0021994 | A1 | 1/2011 | Anderson et al. |
| 2011/0066142 | A1 | 3/2011 | Tal et al. |
| 2011/0071502 | A1 | 3/2011 | Asai |
| 2011/0144620 | A1 | 6/2011 | Tal |
| 2011/0152836 | A1 | 6/2011 | Riopelle et al. |
| 2011/0190778 | A1 | 8/2011 | Arpasi et al. |
| 2011/0202006 | A1 | 8/2011 | Bierman et al. |
| 2011/0230844 | A1 | 9/2011 | Shaw et al. |
| 2011/0251559 | A1 | 10/2011 | Tal et al. |
| 2011/0270192 | A1 | 11/2011 | Anderson et al. |
| 2012/0016346 | A1 | 1/2012 | Steinmetz et al. |
| 2012/0041371 | A1 | 2/2012 | Tal et al. |
| 2012/0065590 | A1 | 3/2012 | Bierman et al. |
| 2012/0078231 | A1 | 3/2012 | Hoshinouchi |
| 2012/0130411 | A1 | 5/2012 | Tal et al. |
| 2012/0130415 | A1 | 5/2012 | Tal et al. |
| 2012/0157854 | A1 | 6/2012 | Kurrus et al. |
| 2012/0215171 | A1 | 8/2012 | Christiansen |
| 2012/0220942 | A1 | 8/2012 | Hall et al. |
| 2012/0226239 | A1 | 9/2012 | Green |
| 2012/0283640 | A1 | 11/2012 | Anderson et al. |
| 2012/0316500 | A1 | 12/2012 | Bierman et al. |
| 2013/0046241 | A1 | 2/2013 | Okamura et al. |
| 2013/0053763 | A1 | 2/2013 | Makino et al. |
| 2013/0053826 | A1 | 2/2013 | Shevgoor |
| 2013/0123704 | A1 | 5/2013 | Bierman et al. |
| 2013/0158338 | A1 | 6/2013 | Kelly et al. |
| 2013/0158506 | A1 | 6/2013 | Harris et al. |
| 2013/0188291 | A1 | 7/2013 | Vardiman |
| 2013/0237931 | A1 | 9/2013 | Tal et al. |
| 2013/0306079 | A1 | 11/2013 | Tracy |
| 2014/0025036 | A1 | 1/2014 | Bierman et al. |
| 2014/0081210 | A1 | 3/2014 | Bierman et al. |
| 2014/0094774 | A1 | 4/2014 | Blanchard |
| 2014/0100552 | A1 | 4/2014 | Gallacher et al. |
| 2014/0110296 | A1 | 4/2014 | Terzibashian |
| 2014/0171833 | A1 | 6/2014 | Matsuno et al. |
| 2014/0188211 | A1 | 7/2014 | Roeder et al. |
| 2014/0207052 | A1 | 7/2014 | Tal et al. |
| 2014/0207069 | A1 | 7/2014 | Bierman et al. |
| 2014/0214005 | A1 | 7/2014 | Belson |
| 2014/0221831 | A1 | 8/2014 | Kurrus et al. |
| 2014/0257111 | A1 | 9/2014 | Yamashita et al. |
| 2014/0276432 | A1 | 9/2014 | Bierman et al. |
| 2014/0276599 | A1 | 9/2014 | Cully et al. |
| 2014/0364766 | A1 | 12/2014 | Devgon et al. |
| 2015/0011834 | A1 | 1/2015 | Ayala et al. |
| 2015/0080939 | A1 | 3/2015 | Adams et al. |
| 2015/0094653 | A1 | 4/2015 | Pacheco et al. |
| 2015/0112307 | A1 | 4/2015 | Margolis |
| 2015/0112310 | A1 | 4/2015 | Call et al. |
| 2015/0119806 | A1 | 4/2015 | Blanchard et al. |
| 2015/0126930 | A1 | 5/2015 | Bierman et al. |
| 2015/0148595 | A1 | 5/2015 | Bagwell et al. |
| 2015/0157829 | A1 | 6/2015 | Bunch et al. |
| 2015/0190168 | A1 | 7/2015 | Bierman et al. |
| 2015/0196210 | A1 | 7/2015 | McCaffrey et al. |
| 2015/0224287 | A1 | 8/2015 | Bian et al. |
| 2015/0231364 | A1 | 8/2015 | Blanchard et al. |
| 2015/0283357 | A1 | 10/2015 | Lampropoulos et al. |
| 2015/0290431 | A1 | 10/2015 | Hall et al. |
| 2015/0297868 | A1 | 10/2015 | Tal et al. |
| 2015/0306356 | A1 | 10/2015 | Gill |

(56) References Cited

U.S. PATENT DOCUMENTS

2015/0320969 A1 11/2015 Haslinger et al.
2015/0320977 A1 11/2015 Vitullo et al.
2015/0351793 A1 12/2015 Bierman et al.
2015/0359549 A1 12/2015 Lenker et al.
2015/0359998 A1 12/2015 Carmel et al.
2016/0001046 A1 1/2016 Tietze
2016/0030716 A1 2/2016 Mallin et al.
2016/0067391 A1 3/2016 Real et al.
2016/0082223 A1 3/2016 Barnell
2016/0114124 A1 4/2016 Tal
2016/0158523 A1 6/2016 Helm
2016/0220786 A1 8/2016 Mitchell et al.
2016/0220811 A1 8/2016 Spotnitz et al.
2016/0242661 A1 8/2016 Fischell et al.
2016/0256101 A1 9/2016 Aharoni et al.
2016/0256667 A1 9/2016 Ribelin et al.
2016/0325073 A1 11/2016 Davies et al.
2016/0331938 A1 11/2016 Blanchard et al.
2016/0338728 A1 11/2016 Tal
2016/0346503 A1 12/2016 Jackson et al.
2017/0028135 A1 2/2017 Fransson et al.
2017/0035990 A1 2/2017 Swift
2017/0072165 A1 3/2017 Lim et al.
2017/0120000 A1 5/2017 Osypka et al.
2017/0120014 A1 5/2017 Harding et al.
2017/0120034 A1 5/2017 Kaczorowski
2017/0128700 A1 5/2017 Roche Rebollo
2017/0156987 A1 6/2017 Babbs et al.
2017/0172653 A1 6/2017 Urbanski et al.
2017/0182293 A1 6/2017 Chhikara et al.
2017/0239443 A1 8/2017 Abitabilo et al.
2017/0259043 A1 9/2017 Chan et al.
2017/0273713 A1 9/2017 Shah et al.
2017/0274182 A1 9/2017 O'Bryan et al.
2017/0296792 A1 10/2017 Ornelas Vargas et al.
2017/0326339 A1 11/2017 Bailey et al.
2017/0361070 A1 12/2017 Hivert
2017/0368255 A1* 12/2017 Provost ................ G02B 27/425
2018/0001062 A1 1/2018 O'Carrol et al.
2018/0008294 A1 1/2018 Garrison et al.
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0214674 A1 8/2018 Ebnet et al.
2018/0229004 A1 8/2018 Blanchard et al.
2018/0296799 A1 10/2018 Horst et al.
2018/0296804 A1 10/2018 Bierman
2018/0310955 A1 11/2018 Lindekugel et al.
2018/0369540 A1 12/2018 Asai
2019/0015646 A1 1/2019 Matlock et al.
2019/0021640 A1 1/2019 Burkholz et al.
2019/0038113 A1 2/2019 Chu
2019/0060616 A1 2/2019 Solomon
2019/0076167 A1 3/2019 Fantuzzi et al.
2019/0076628 A1 3/2019 Anstett
2019/0134349 A1 5/2019 Cohn et al.
2019/0192824 A1 6/2019 Cordeiro et al.
2019/0201665 A1 7/2019 Turpin
2019/0209812 A1 7/2019 Burkholz et al.
2019/0240459 A1 8/2019 Belson
2019/0255294 A1 8/2019 Mitchell et al.
2019/0255298 A1 8/2019 Mitchell et al.
2019/0275303 A1 9/2019 Tran et al.
2019/0276268 A1 9/2019 Akingba
2019/0282788 A1 9/2019 Stone et al.
2019/0321590 A1 10/2019 Burkholz et al.
2019/0351196 A1 11/2019 Ribelin et al.
2020/0001051 A1 1/2020 Huang et al.
2020/0016374 A1 1/2020 Burkholz et al.
2020/0046948 A1 2/2020 Burkholz et al.
2020/0100716 A1 4/2020 Devgon et al.
2020/0129732 A1 4/2020 Vogt et al.
2020/0147349 A1 5/2020 Holt
2020/0197579 A1 6/2020 Chu et al.
2020/0197682 A1* 6/2020 Franklin ........... A61M 25/0097
2020/0197684 A1 6/2020 Wax
2020/0237278 A1 7/2020 Asbaghi
2020/0359995 A1 11/2020 Walsh et al.
2021/0030944 A1 2/2021 Cushen et al.
2021/0060306 A1 3/2021 Kumar
2021/0069471 A1 3/2021 Howell
2021/0085927 A1 3/2021 Howell
2021/0100985 A1 4/2021 Akcay et al.
2021/0113809 A1 4/2021 Howell
2021/0113810 A1 4/2021 Howell
2021/0113816 A1 4/2021 DiCianni
2021/0121661 A1 4/2021 Howell
2021/0121667 A1 4/2021 Howell
2021/0228842 A1 7/2021 Scherich et al.
2021/0228843 A1 7/2021 Howell et al.
2021/0244920 A1 8/2021 Kujawa et al.
2021/0290898 A1 9/2021 Burkholz
2021/0290901 A1 9/2021 Burkholz et al.
2021/0290913 A1 9/2021 Horst et al.
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001109 A1 1/2022 Simon
2022/0001138 A1 1/2022 Howell
2022/0032013 A1 2/2022 Howell et al.
2022/0032014 A1 2/2022 Howell et al.
2022/0062528 A1 3/2022 Thornley et al.
2022/0062596 A1 3/2022 Ribelin et al.
2022/0126064 A1 4/2022 Tobin et al.
2022/0193376 A1 6/2022 Spataro et al.
2022/0193377 A1 6/2022 Haymond et al.
2022/0193378 A1 6/2022 Spataro et al.
2022/0203075 A1* 6/2022 Murphy .......... A61M 25/09041
2022/0323723 A1 10/2022 Spataro et al.
2022/0331562 A1 10/2022 Jaros et al.
2022/0331563 A1 10/2022 Papadia
2023/0042898 A1 2/2023 Howell et al.
2023/0096377 A1 3/2023 West et al.
2023/0096740 A1 3/2023 Bechstein et al.
2023/0099654 A1 3/2023 Blanchard et al.
2023/0100482 A1 3/2023 Howell
2023/0102231 A1 3/2023 Bechstein et al.
2023/0173231 A1 6/2023 Parikh et al.
2023/0233814 A1 7/2023 Howell et al.
2023/0381459 A1 11/2023 Belson et al.
2023/0381481 A1 11/2023 Pizzato
2024/0009427 A1 1/2024 Howell et al.
2024/0050706 A1 2/2024 Howell et al.
2024/0198058 A1 6/2024 Howell et al.
2025/0001136 A1 1/2025 Mitchell et al.
2025/0065083 A1 2/2025 Haymond et al.
2025/0082906 A1 3/2025 Howell et al.
2025/0222237 A1 7/2025 Spataro et al.
2025/0235669 A1 7/2025 Howell

FOREIGN PATENT DOCUMENTS

EP 0730880 A1 9/1996
EP 2061385 A1 5/2009
EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012
EP 2152348 B1 2/2015
EP 3473291 A1 4/2019
EP 3093038 B1 5/2019
EP 2260897 B1 9/2019
EP 3693051 A1 8/2020
GB 1273547 A 5/1972

(56) References Cited

FOREIGN PATENT DOCUMENTS

| | | | |
|---|---|---|---|
| JP | 2004248987 | A | 9/2004 |
| JP | 2008054859 | A | 3/2008 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 9857685 | A1 | 12/1998 |
| WO | 99/12600 | A1 | 3/1999 |
| WO | 99/26681 | A1 | 6/1999 |
| WO | 00/06221 | A1 | 2/2000 |
| WO | 0054830 | A1 | 9/2000 |
| WO | 2003008020 | A1 | 1/2003 |
| WO | 2003057272 | A2 | 7/2003 |
| WO | 03/068073 | A1 | 8/2003 |
| WO | 2003066125 | A2 | 8/2003 |
| WO | 2005096778 | A2 | 10/2005 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011109792 | A1 | 9/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012/154277 | A1 | 11/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015077560 | A1 | 5/2015 |
| WO | 2015168655 | A2 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016/187063 | A1 | 11/2016 |
| WO | 2016176065 | A1 | 11/2016 |
| WO | 2016178974 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019/146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020/113123 | A1 | 6/2020 |
| WO | 2020109448 | A1 | 6/2020 |
| WO | 2021038041 | A1 | 3/2021 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2021226050 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

PCT/US2021/057135 filed Oct. 28, 2021 International Search Report and Written Opinion dated Mar. 11, 2022.

PCT/US2021/064671 filed Dec. 21, 2021 International Search Report and Written Opinion dated May 27, 2022.

PCT/US2022/039614 filed Aug. 5, 2022 International Search Report and Written Opinion dated Dec. 22, 2022.

PCT/US2022/044848 filed Sep. 27, 2022 International Search Report and Written Opinion dated Feb. 3, 2023.

PCT/US2022/044879 filed Sep. 27, 2022 International Search Report and Written Opinion dated Mar. 3, 2023.

PCT/US2022/044901 filed Sep. 27, 2022 International Search Report and Written Opinion dated Mar. 3, 2023.

PCT/US2022/044918 filed Sep. 27, 2022 International Search Report and Written Opinion dated Feb. 21, 2023.

PCT/US2022/044923 filed Sep. 27, 2022 International Search Report and Written Opinion dated Feb. 15, 2023.

PCT/US2023/011173 filed Jan. 19, 2023 International Search Report and Written Opinion dated May 22, 2023.

U.S. Appl. No. 16/398,020, filed Apr. 29, 2019 Examiner's Answer dated Oct. 31, 2022.

U.S. Appl. No. 17/156,252, filed Jan. 22, 2021 Non-Final Office Action dated Oct. 25, 2022.

U.S. Appl. No. 17/156,252, filed Jan. 22, 2021 Notice of Allowance dated Apr. 24, 2023.

U.S. Appl. No. 17/237,909, filed Apr. 22, 2021 Restriction Requirement dated Feb. 1, 2023.

U.S. Appl. No. 17/240,591, filed Apr. 26, 2021 Non-Final Office Action dated Jun. 8, 2023.

U.S. Appl. No. 17/326,017, filed May 20, 2021 Non-Final Office Action dated Jan. 26, 2023.

U.S. Appl. No. 17/358,504, filed Jun. 25, 2021 Restriction Requirement dated Jun. 7, 2023.

U.S. Appl. No. 17/390,682, filed Jul. 30, 2021 Non-Final Office Action dated Mar. 2, 2023.

U.S. Appl. No. 17/392,061, filed Aug. 2, 2021 Restriction Requirement dated Mar. 30, 2023.

U.S. Appl. No. 17/360,694, filed Jun. 28, 2021 Notice of Allowance dated Dec. 16, 2024.

U.S. Appl. No. 17/392,061, filed Aug. 2, 2021 Final Office Action dated Jan. 2, 2025.

U.S. Appl. No. 17/461,619, filed Aug. 30, 2021 Non-Final Office Action dated Feb. 11, 2025.

U.S. Appl. No. 17/461,619, filed Aug. 30, 2021 Restriction Requirement dated Dec. 6, 2024.

U.S. Appl. No. 17/513,789, filed Oct. 28, 2021 Notice of Allowance dated Jan. 3, 2025.

U.S. Appl. No. 17/557,924, filed Dec. 21, 2021 Notice of Allowance dated Dec. 11, 2024.

U.S. Appl. No. 17/390,682, filed Jul. 30, 2021 Notice of Allowance dated Dec. 15, 2025.

U.S. Appl. No. 17/392,061, filed Aug. 2, 2021 Notice of Allowance dated Oct. 27, 2025.

U.S. Appl. No. 17/461,619, filed Aug. 30, 2021 Advisory Action dated Aug. 14, 2025.

U.S. Appl. No. 17/461,619, filed Aug. 30, 2021 Final Office Action dated Jun. 2, 2025.

(56) References Cited

OTHER PUBLICATIONS

U.S. Appl. No. 17/461,619, filed Aug. 30, 2021 Non-Final Office Action dated Oct. 7, 2025.
U.S. Appl. No. 17/716,675, filed Apr. 8, 2022 Non-Final Office Action dated Sep. 11, 2025.
U.S. Appl. No. 17/716,675, filed Apr. 8, 2022 Restriction Requirement dated Jul. 2, 2025.
U.S. Appl. No. 17/882,388, filed Aug. 5, 2022 Non-Final Office Action dated Aug. 20, 2025.
U.S. Appl. No. 17/953,860, filed Sep. 27, 2022 Restriction Requirement dated Oct. 22, 2025.
U.S. Appl. No. 17/953,959, filed Sep. 27, 2022 Restriction Requirement dated Oct. 22, 2025.
U.S. Appl. No. 17/954,096, filed Sep. 27, 2022 Non-Final Office Action dated Aug. 26, 2025.
U.S. Appl. No. 17/954,132, filed Sep. 27, 2022 Non-Final Office Action dated Aug. 21, 2025.
U.S. Appl. No. 18/099,185, filed Jan. 19, 2023 Non-Final Office Action dated Dec. 2, 2025.
U.S. Appl. No. 18/372,610, filed Sep. 25, 2023 Notice of Allowance dated Dec. 16, 2025.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Final Office Action dated Mar. 13, 2024.
U.S. Appl. No. 17/390,682, filed July 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Final Office Action dated Jul. 9, 2024.
U.S. Appl. No. 17/554,978, filed Dec. 17, 2021 Non-Final Office Action dated Apr. 19, 2024.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/326,017, filed May 20, 2021 Notice of Allowance dated Jul. 3, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
U.S. Appl. No. 16/398,020, filed Apr. 29, 2019 Board Decision dated Oct. 30, 2023.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Restriction Requirement dated Oct. 3, 2023.
U.S. Appl. No. 17/557,924, filed Dec. 21, 2021 Non-Final Office Action dated Nov. 3, 2023.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/358,504, filed Jun. 25, 2021 Notice of Allowance dated Jul. 17, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
PCT/US2020/052536 filed Sep. 24, 2020 International Search Report and Written Opinion dated Dec. 4, 2020.
PCT/US2021/014700 filed Jan. 22, 2021 International Search Report and Written Opinion dated Jun. 29, 2021.
PCT/US2021/028018 filed Apr. 19, 2021 International Preliminary Report on Patentability dated Jun. 3, 2022.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2022/024085 filed Apr. 8, 2022 International Search Report and Wirtten Opinion dated Sep. 12, 2022.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
U.S. Appl. No. 17/031,478, filed Sep. 24, 2020 Notice of Allowance dated Sep. 16, 2022.
U.S. Appl. No. 17/234,611, filed Apr. 19, 2021 Examiner's Answer dated May 1, 2025.
U.S. Appl. No. 17/390,682, filed Jul. 30, 2021 Final Office Action dated Feb. 28, 2025.
U.S. Appl. No. 17/392,061, filed Aug. 2, 2021 Advisory Action dated Mar. 12, 2025.
U.S. Appl. No. 17/392,061, filed Aug. 2, 2021 Non-Final Office Action dated Apr. 5, 2025.
U.S. Appl. No. 17/558,124, filed Dec. 21, 2021 Notice of Allowance dated Mar. 7, 2025.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.

(56) References Cited

OTHER PUBLICATIONS

U.S. Appl. No. 17/360,694, filed Jun. 28, 2021 Non-Final Office Action dated Feb. 14, 2024.
U.S. Appl. No. 17/392,061, filed Aug. 2, 2021 Advisory Action dated Feb. 14, 2024.
U.S. Appl. No. 17/513,789, filed Oct. 28, 2021 Non-Final Office Action dated Jan. 9, 2024.
U.S. Appl. No. 17/557,924, filed Dec. 21, 2021 Final Office Action dated Feb. 29, 2024.
U.S. Appl. No. 17/234,611, filed Apr. 19, 2021 Board Decision dated Jan. 23, 2026.
U.S. Appl. No. 17/240,591, filed Apr. 26, 2021 Board Decision dated Feb. 18, 2026.
U.S. Appl. No. 17/240,591, filed Apr. 26, 2021 Notice of Allowance dated Mar. 25, 2026.
U.S. Appl. No. 17/461,619, filed Aug. 30, 2021 Final Office Action dated Feb. 10, 2026.
U.S. Appl. No. 17/716,675, filed Apr. 8, 2022 Non-Final Office Action dated Mar. 9, 2026.
U.S. Appl. No. 17/882,388, filed Aug. 5, 2022 Final Office Action dated Jan. 12, 2026.
U.S. Appl. No. 17/882,388, filed Aug. 5, 2022 Notice of Allowance dated Apr. 13, 2026.
U.S. Appl. No. 17/953,860, filed Sep. 27, 2022 Non-Final Office Action dated Jan. 29, 2026.
U.S. Appl. No. 17/953,959, filed Sep. 27, 2022 Non-Final Office Action dated Mar. 30, 2026.
U.S. Appl. No. 17/954,096, filed Sep. 27, 2022 Final Office Action dated Feb. 10, 2026.
U.S. Appl. No. 17/954,096, filed Sep. 27, 2022 Notice of Allowance dated Apr. 23, 2026.
U.S. Appl. No. 17/954,132, filed Sep. 27, 2022 Final Office Action dated Mar. 4, 2026.
U.S. Appl. No. 18/075,261, filed Dec. 5, 2022 Non-Final Office Action dated Apr. 22, 2026.
U.S. Appl. No. 18/099,185, filed Jan. 19, 2023 Final Office Action dated Apr. 20, 2026.
U.S. Appl. No. 18/383,814, filed Oct. 25, 2023 Non-Final Office Action dated Apr. 17, 2026.
U.S. Appl. No. 18/383,814, filed Oct. 25, 2023 Restriction Requirement dated Jan. 22, 2026.
U.S. Appl. No. 18/593,431, filed Mar. 1, 2024 Non-Final Office Action dated Apr. 21, 2026.

* cited by examiner

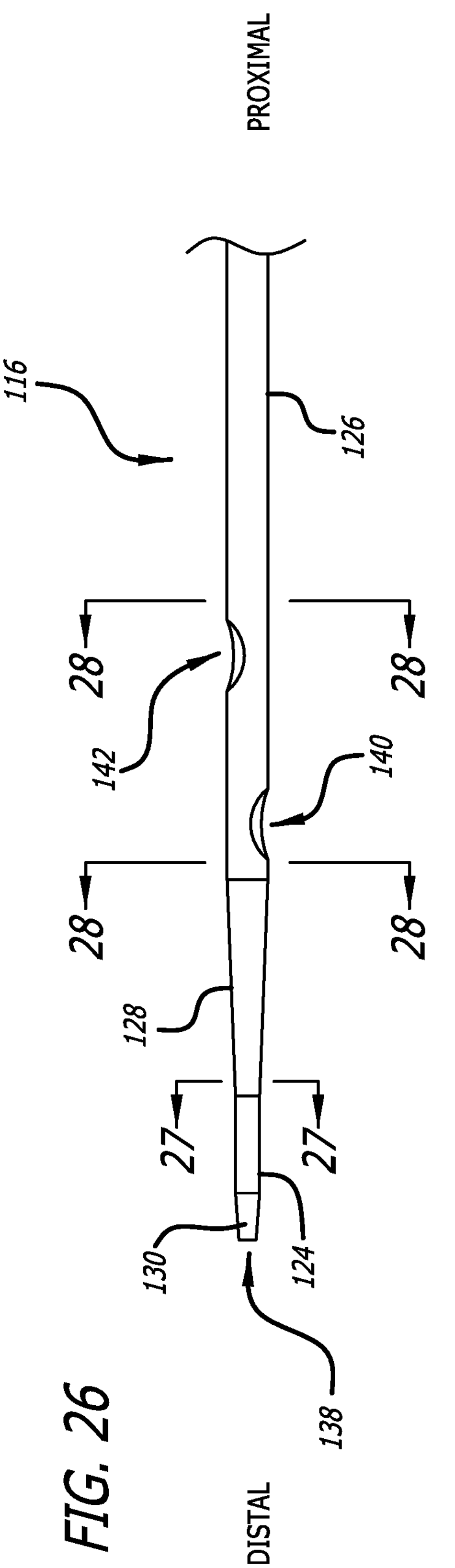
FIG. 26
FIG. 28
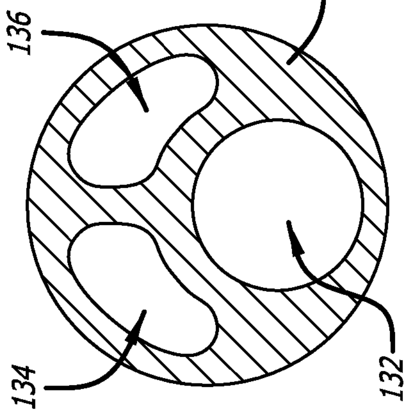
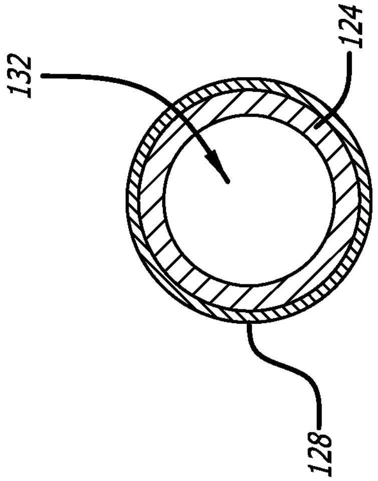
FIG. 27

COMPACT INSERTION ASSEMBLIES OF RAPIDLY INSERTABLE CENTRAL CATHETERS AND METHODS THEREOF

PRIORITY

This application claims the benefit of priority to U.S. Provisional Application No. 63/249,009, filed Sep. 27, 2021, and to U.S. Provisional Application No. 63/271,043, filed Oct. 22, 2021, each of which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps can be time consuming, handling the number of medical devices can be awkward, and both of the foregoing can lead to patient trauma. In addition, there is a relatively high potential for touch contamination due to the number of medical devices that need to be interchanged during the Seldinger technique. Unfortunately, this is complicated by many of the foregoing medical devices being unwieldy elongate medical devices, which further increases the relatively high potential for touch contamination. As such, there is a need to reduce the number of steps and medical devices involved in introducing a catheter such as a CVC into a patient, as well as a need to reduce the unwieldiness of the foregoing medical devices.

Disclosed herein are compact rapidly insertable central catheters ("RICC") insertion assemblies and methods thereof that address at least the foregoing needs.

SUMMARY

Disclosed herein is RICC insertion assembly including, in some embodiments, a RICC, an introducer assembly, an access guidewire, and a coupler coupling together the RICC and the introducer assembly, the RICC and the access guidewire, or the introducer assembly and the access guidewire. The RICC includes a catheter tube, a catheter hub coupled to a proximal portion of the catheter tube, and one or more extension legs. Each extension leg of the one-or-more extension legs coupled to the catheter hub by a distal portion thereof. The introducer assembly includes a syringe and an introducer needle coupled to the syringe. The introducer needle includes a needle shaft and a needle hub over a proximal portion of the needle shaft. The needle hub includes a needle-hub through hole passing through a side of the needle hub and connecting to a needle-shaft lumen. The access guidewire includes a proximal portion disposed in a primary lumen of the RICC and a distal portion disposed in the needle-shaft lumen by way of the needle-hub through hole.

In some embodiments, the coupler coupling together the RICC and the introducer assembly enforces a loop in the access guidewire over which the catheter tube follows.

In some embodiments, the coupler includes a clip and a seat opposite the clip. The clip clips onto a barrel of the syringe. The seat seats the catheter hub thereon.

In some embodiments, the coupler includes a clip and a seat opposite the clip. The clip clips onto the needle hub. The seat seats the catheter hub thereon.

In some embodiments, the seat includes posts extending therefrom. The posts insert into suture-wing holes of suture wings extending from the catheter hub, thereby securing the catheter hub on the seat.

In some embodiments, the clip and the seat are fixed with respect to each other. The coupler orients the catheter hub in either a longitudinal or transverse orientation with respect to a central axis of the introducer assembly.

In some embodiments, the clip and the seat include a Hirth-like joint therebetween. The coupler allows a clinician to orient the catheter hub in any clinician-desired orientation thereof with respect to a central axis of the introducer assembly.

In some embodiments, the coupler is an access-guidewire hub coupled to a proximal end of the access guidewire. In addition, the access-guidewire hub is coupled to another side of the needle hub opposite that including the needle-hub through hole. Lastly, the access-guidewire hub screws onto an extension-leg connector extending from a proximal portion of an extension leg of the one-or-more extension legs.

In some embodiments, the coupler coupling together the RICC and the access guidewire enforces a loop in the access guidewire over which the catheter tube follows.

In some embodiments, the coupler includes a clip and a seat opposite the clip. The clip clips onto the access guidewire. The seat seats the catheter hub thereon.

In some embodiments, the clip is a groove in the coupler.

In some embodiments, the seat includes posts extending therefrom. The posts insert into suture-wing holes of suture wings extending from the catheter hub, thereby securing the catheter hub on the seat.

In some embodiments, the coupler includes a clip integrated into a patient-facing side of the catheter hub. The clip clips onto the access guidewire.

In some embodiments, the clip is a groove in the catheter hub.

In some embodiments, the coupler includes a clip or releasable tie around the catheter tube of the RICC and the access guidewire.

In some embodiments, the coupler coupling together the introducer assembly and the access guidewire includes a clip or releasable tie around a barrel of the syringe and the access guidewire.

In some embodiments, the coupler coupling together the introducer assembly and the access guidewire includes a rotatable lever of a coupler-housing lock of a housing of the coupler. The coupler-housing lock has a locked state and an unlocked state respectively for locking and unlocking the needle hub from a distal coupler-housing piece of the coupler housing.

In some embodiments, the locked state and the unlocked state of the coupler-housing lock are further respectively for clamping and unclamping the access guidewire.

In some embodiments, the needle-hub through hole includes a gasket disposed therein. The gasket is configured to seal around the access guidewire and allow a vacuum to be drawn with the syringe without leaking through the needle-hub through hole.

In some embodiments, the gasket includes one or more 'O'-rings.

In some embodiments, the RICC includes a set of three lumens including the primary lumen, a secondary lumen, and a tertiary lumen. The set of three lumens is formed of fluidly connected portions of three catheter-tube lumens, three catheter-hub lumens, and three extension-leg lumens.

In some embodiments, the primary lumen has a primary-lumen aperture in a distal end of the catheter tube. The secondary lumen has a secondary-lumen aperture in a side of the distal portion of catheter tube. The tertiary lumen has a tertiary-lumen aperture in the side of the distal portion of the catheter tube proximal of the secondary-lumen aperture.

In some embodiments, the RICC insertion assembly is in a ready-to-deploy state thereof with a guidewire tip of the access guidewire disposed just proximal of a needle tip of the needle.

In some embodiments, the guidewire tip is straight in the needle-shaft lumen in the ready-to-deploy state of the RICC insertion assembly but adopts a 'J' shape when advanced beyond the needle tip in a deployed state of the RICC insertion assembly.

Also disclosed herein is an introducer needle including, in some embodiments, a needle shaft and a needle hub over a proximal portion of the needle shaft. The needle hub includes a needle-hub through hole passing through a side of the needle hub and connecting to a needle-shaft lumen. The needle-hub through hole is configured to pass an access guidewire therethrough.

In some embodiments, the needle-hub through hole includes a gasket disposed therein. The gasket is configured to seal around the access guidewire and allow a vacuum to be drawn with a syringe without leaking through the needle-hub through hole.

In some embodiments, the gasket includes one or more 'O'-rings.

Also disclosed herein is a method of a RICC insertion assembly. The method includes, in some embodiments, an assembly-obtaining step, a needle tract-establishing step, and an access guidewire-advancing step. The assembly-obtaining step includes obtaining a RICC insertion assembly. The RICC insertion assembly includes, in a ready-to-deploy state thereof, a RICC, an introducer assembly, an access guidewire, and a coupler coupling together the RICC and the introducer assembly. The introducer assembly includes a syringe coupled to an introducer needle. The introducer needle includes a needle hub over a proximal portion of a needle shaft. The access guidewire includes a proximal portion disposed in a primary lumen of the RICC. The access guidewire also includes a distal portion disposed in a needle-shaft lumen of the needle shaft by way of a needle-hub through hole passing through a side of the needle hub. The coupler, by coupling together the RICC and the introducer assembly, enforces a loop in the access guidewire over which the catheter tube follows. The needle tract-establishing step includes establishing a needle tract from an area of skin to a blood-vessel lumen of a patient with the introducer needle. The access guidewire-advancing step includes advancing a distal end of the access guidewire into the blood-vessel lumen from its initial location in the needle-shaft lumen just proximal of a needle tip of the needle shaft. The access guidewire-advancing step secures access to the blood-vessel lumen with the access guidewire.

In some embodiments, the method further includes an assembly-adjusting step. The assembly-adjusting step includes adjusting the RICC insertion assembly to be in the ready-to-deploy state thereof before the establishing of the needle tract if the RICC insertion assembly is not already in the ready-to-deploy state upon the obtaining of the RICC insertion assembly in the assembly-obtaining step.

In some embodiments, the needle tract-establishing step includes ensuring blood flashes back into the needle hub of the introducer needle, a syringe tip of the syringe, a barrel of the syringe, or a combination thereof. The ensuring of the blood flashing back into the needle hub of the introducer needle, the syringe tip of the syringe, the barrel of the syringe, or the combination thereof confirms the needle tract extends into the blood-vessel lumen.

In some embodiments, the needle tract-establishing step includes drawing a slight vacuum with the syringe while establishing the needle tract for the ensuring of the blood flashing back into the needle hub of the introducer needle, the syringe tip of the syringe, the barrel of the syringe, or the combination thereof.

In some embodiments, the method further includes a blood-aspirating step. The blood-aspirating step includes aspirating blood with the syringe for confirmation the needle tract extends into the blood-vessel lumen. The needle-hub through hole includes a gasket disposed therein forming a seal around the access guidewire. The seal allows a vacuum to be drawn with the syringe for the aspirating of the blood with the syringe during the blood-aspirating step.

In some embodiments, the advancing of the distal end of the access guidewire into the blood-vessel lumen simultaneously reduces a size of the loop with the advancing of the access guidewire during the access guidewire-advancing step.

In some embodiments, the method further includes an introducer needle-withdrawing step. The introducer needle-withdrawing step includes withdrawing the introducer needle from the patient leaving the access guidewire in place in the blood-vessel lumen.

In some embodiments, the method further includes a catheter tube-advancing step. The catheter tube-advancing step includes advancing a catheter tube of the RICC over the access guidewire and into the blood-vessel lumen. The catheter tube-advancing step places the RICC in the blood-vessel lumen.

In some embodiments, the method further includes an access guidewire-withdrawing step. The access guidewire-withdrawing step includes withdrawing the access guidewire leaving the catheter tube in place in the blood-vessel lumen.

In some embodiments, the method further includes a maneuver guidewire-advancing step, an additional catheter tube-advancing step, and a maneuver guidewire-withdrawing step. The maneuver guidewire-advancing step includes advancing a maneuver guidewire into the blood-vessel lumen by way of the primary lumen of the RICC. The additional catheter tube-advancing step includes advancing a distal portion of the catheter tube farther into the blood-vessel lumen over the maneuver guidewire to a lower ⅓ of a superior vena cava ("SVC") of a heart of the patient. The maneuver guidewire-withdrawing step includes withdrawing the maneuver guidewire leaving the catheter tube in place in the lower ⅓ of the SVC.

These and other features of the concepts provided herein will become more apparent to those of skill in the art in view of the accompanying drawings and following description, which describe particular embodiments of such concepts in greater detail.

DRAWINGS

FIG. 26 illustrates a detailed view of a distal portion of the catheter tube of the RICC in accordance with some embodiments.

FIG. 27 illustrates a first transverse cross section of the distal portion of the catheter tube in accordance with some embodiments.

FIG. 28 illustrates a second or third transverse cross section of the distal portion of the catheter tube in accordance with some embodiments.

DESCRIPTION

Figure 1:
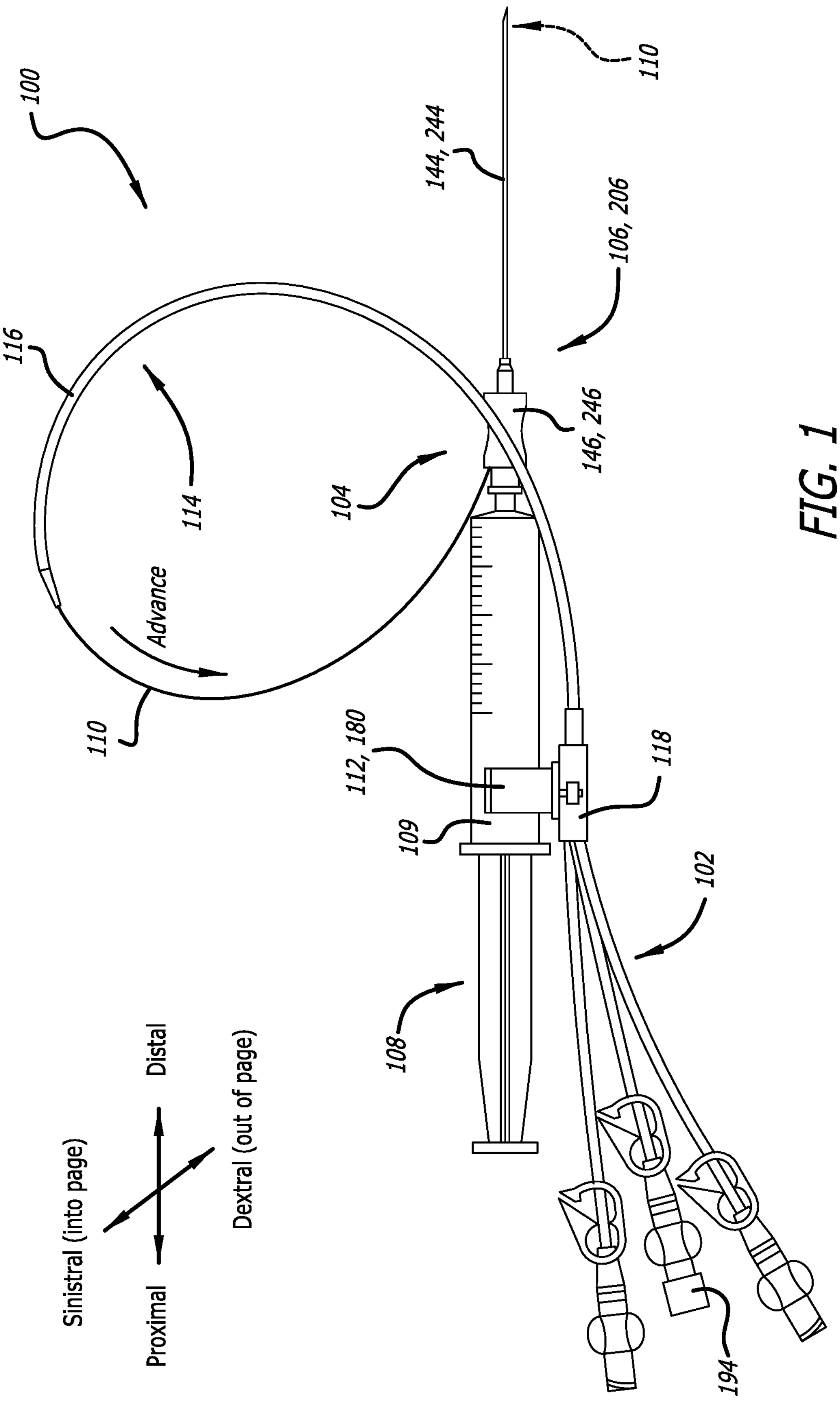
FIG. 1 illustrates a RICC insertion assembly in a ready-to-deploy state thereof with a first coupler coupling together a catheter hub of a RICC and a barrel of a syringe of an introducer assembly to enforce a loop in an access guidewire of a first configuration in accordance with some embodiments.
Figure 2:
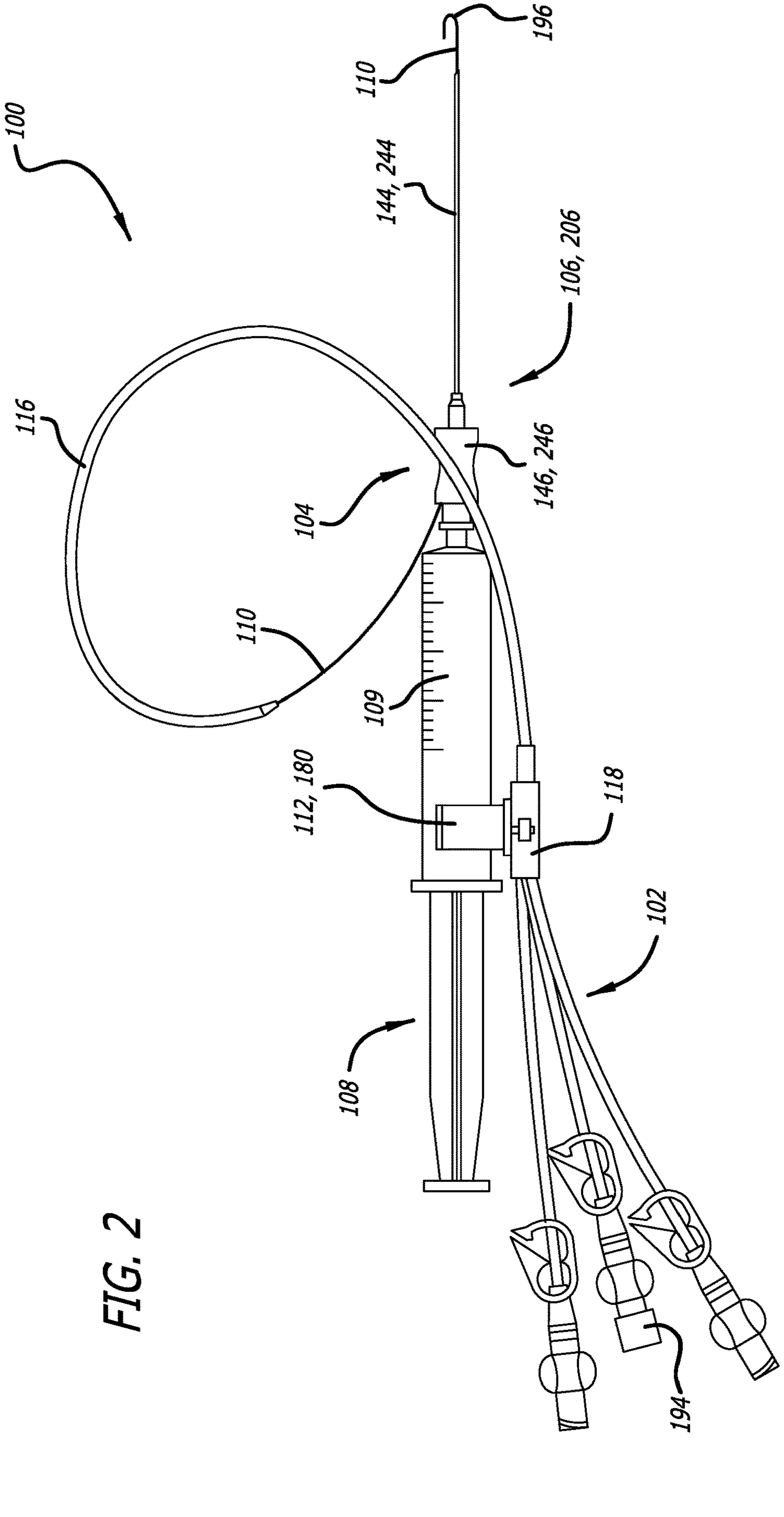
FIG. 2 illustrates the RICC insertion assembly of FIG. 1 in a deployed state thereof in accordance with some embodiments.
Figure 3:
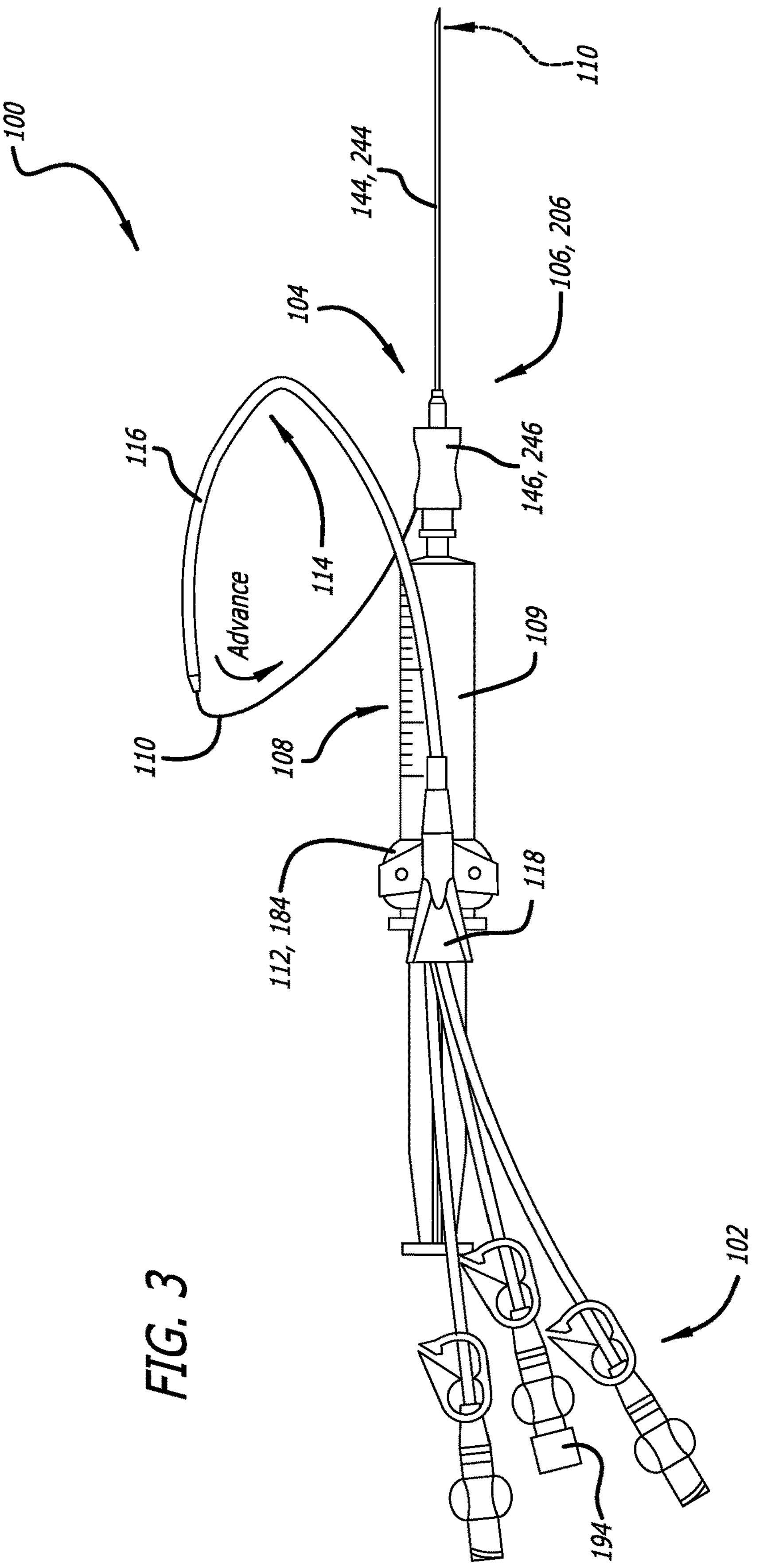
FIG. 3 illustrates the RICC insertion assembly in a ready-to-deploy state thereof with the coupler coupling together the catheter hub of the RICC and the barrel of the syringe of the introducer assembly to enforce a loop in the access guidewire of a second configuration in accordance with some embodiments.
Figure 4:
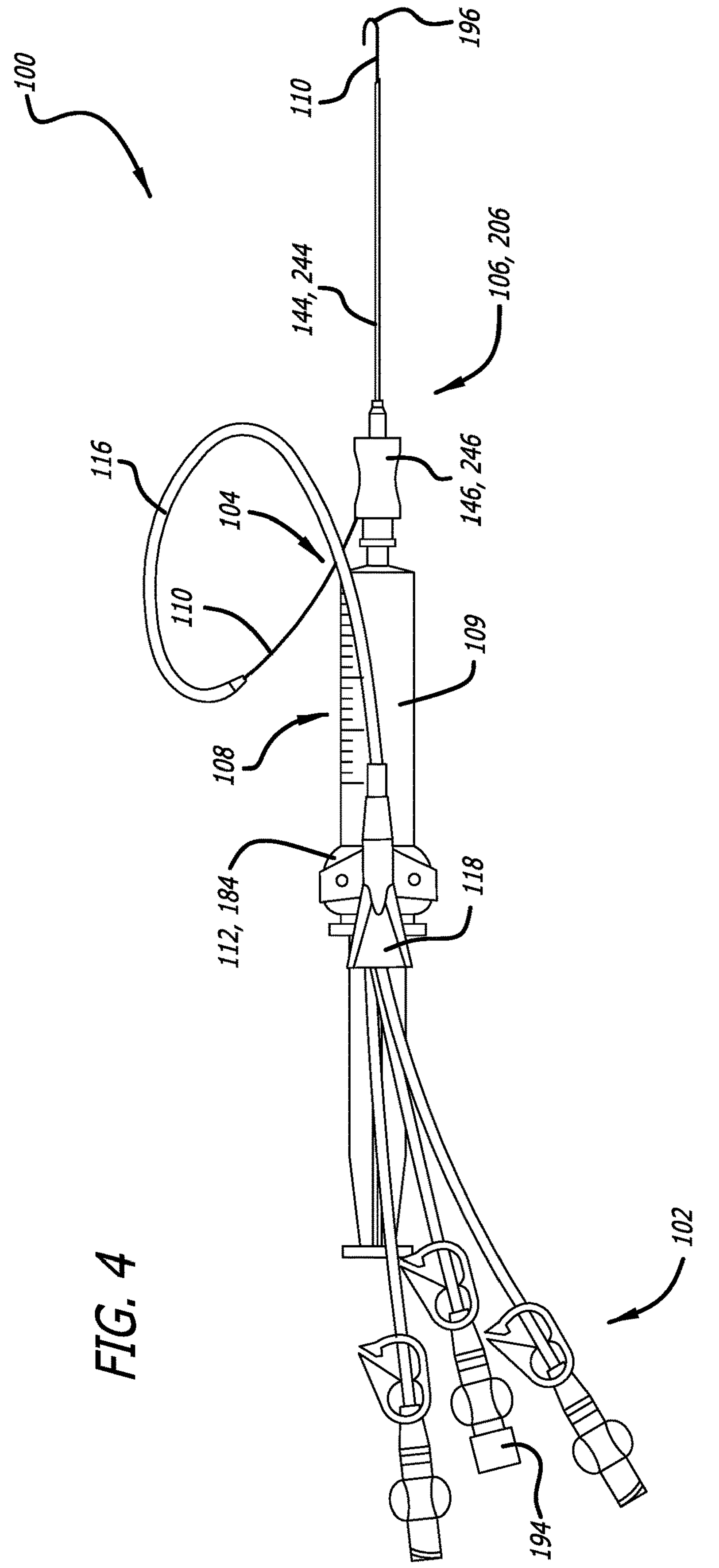
FIG. 4 illustrates the RICC insertion assembly of FIG. 3 in a deployed state thereof in accordance with some embodiments.
Figure 5:
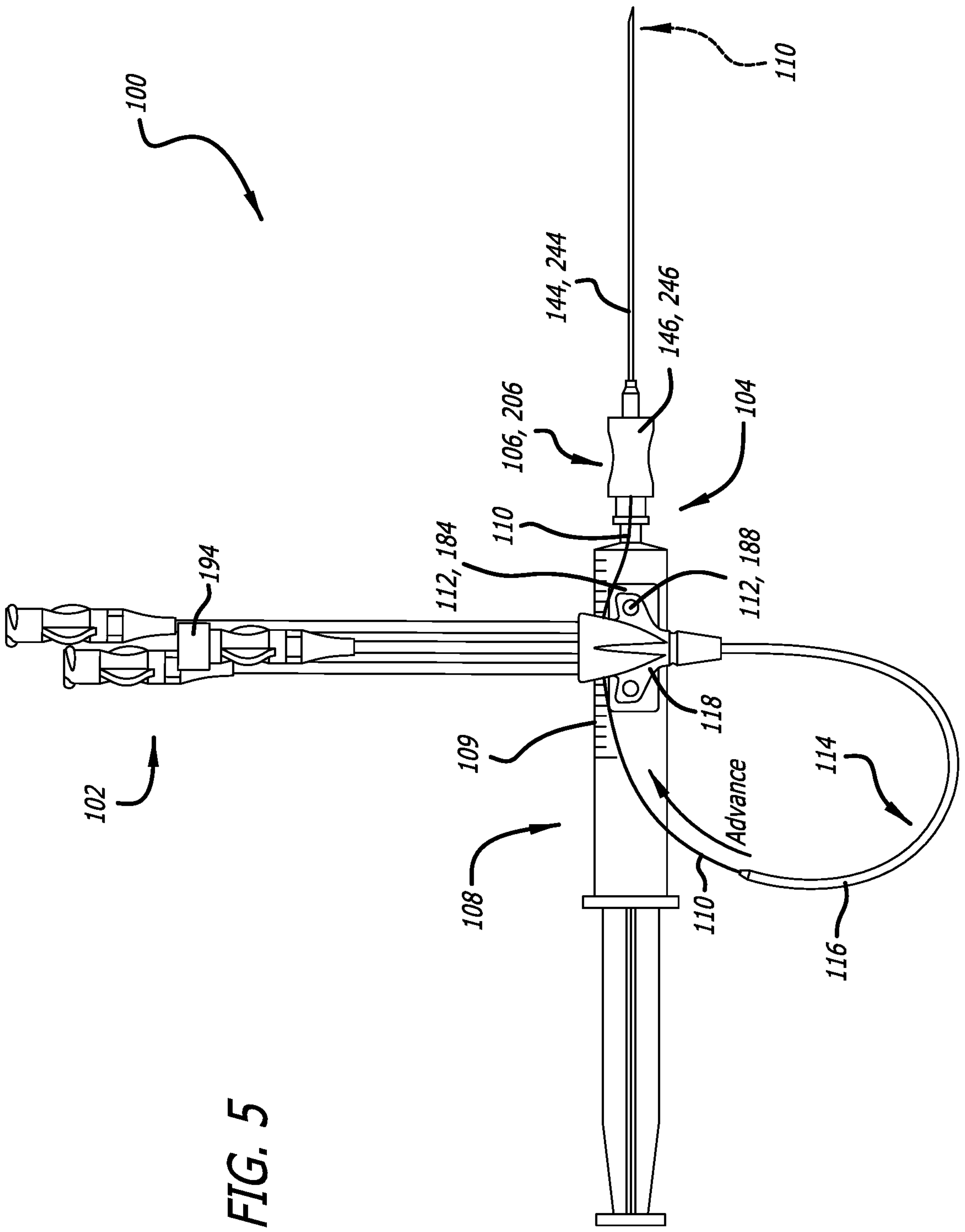
FIG. 5 illustrates the RICC insertion assembly in a ready-to-deploy state thereof with the first coupler coupling together the catheter hub of the RICC and the barrel of the syringe of the introducer assembly to enforce a loop in an access guidewire of a third configuration in accordance with some embodiments.
Figure 6:
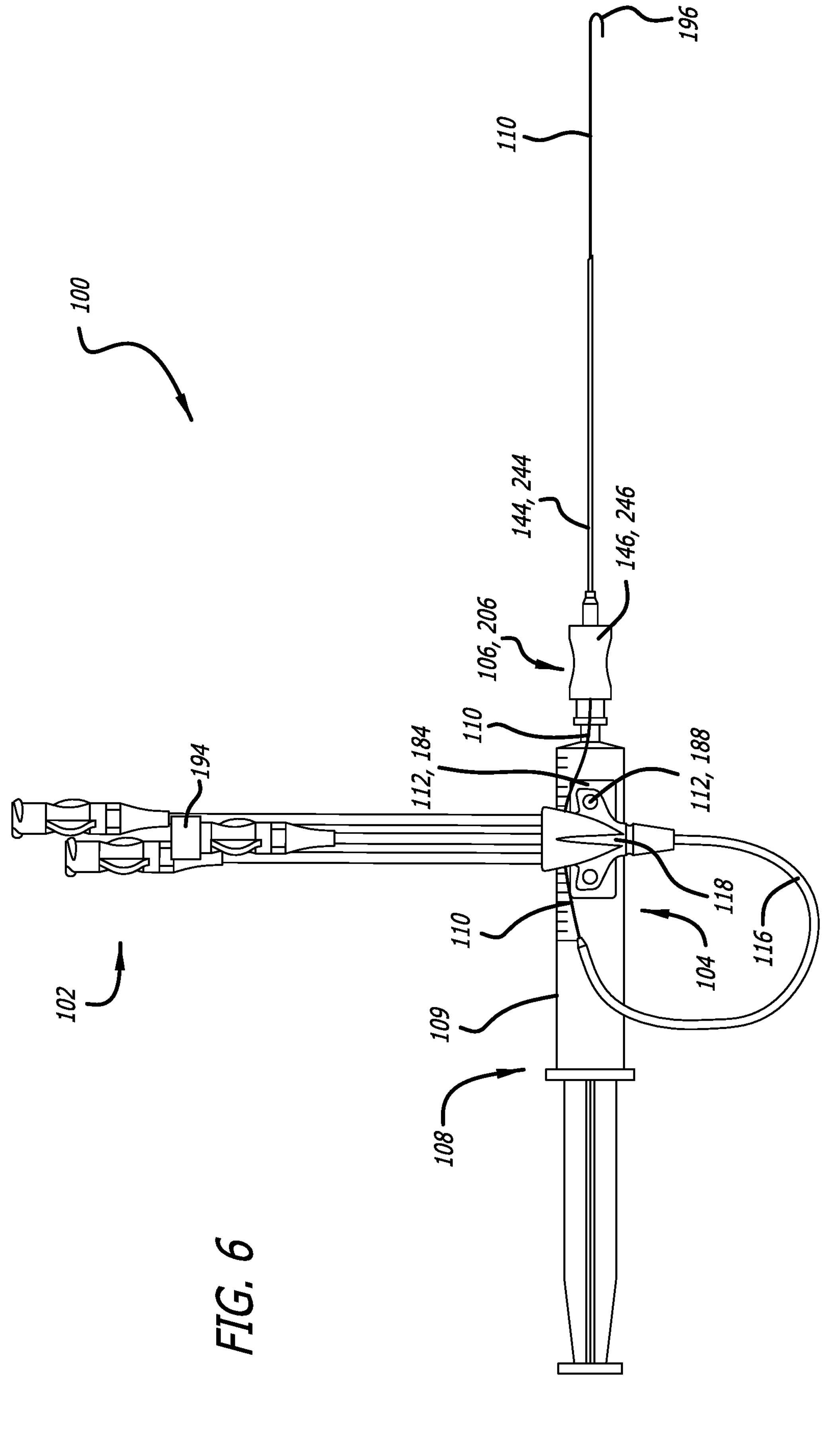
FIG. 6 illustrates the RICC insertion assembly of FIG. 5 in a deployed state thereof in accordance with some embodiments.
Figure 7:
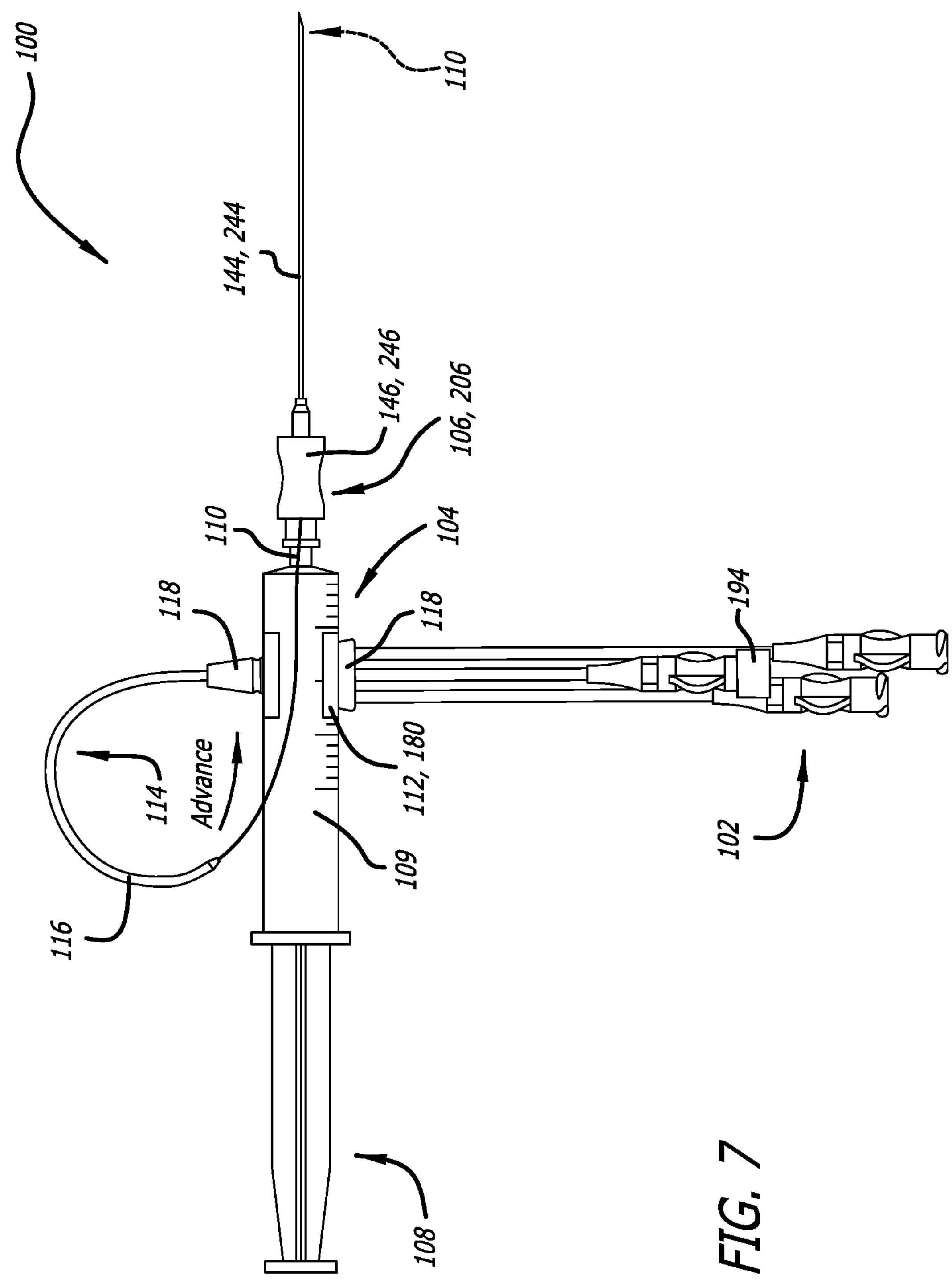
FIG. 7 illustrates the RICC insertion assembly in a ready-to-deploy state thereof with the first coupler coupling together the catheter hub of the RICC and the barrel of the syringe of the introducer assembly to enforce a loop in the access guidewire of a fourth configuration in accordance with some embodiments.
Figure 8:
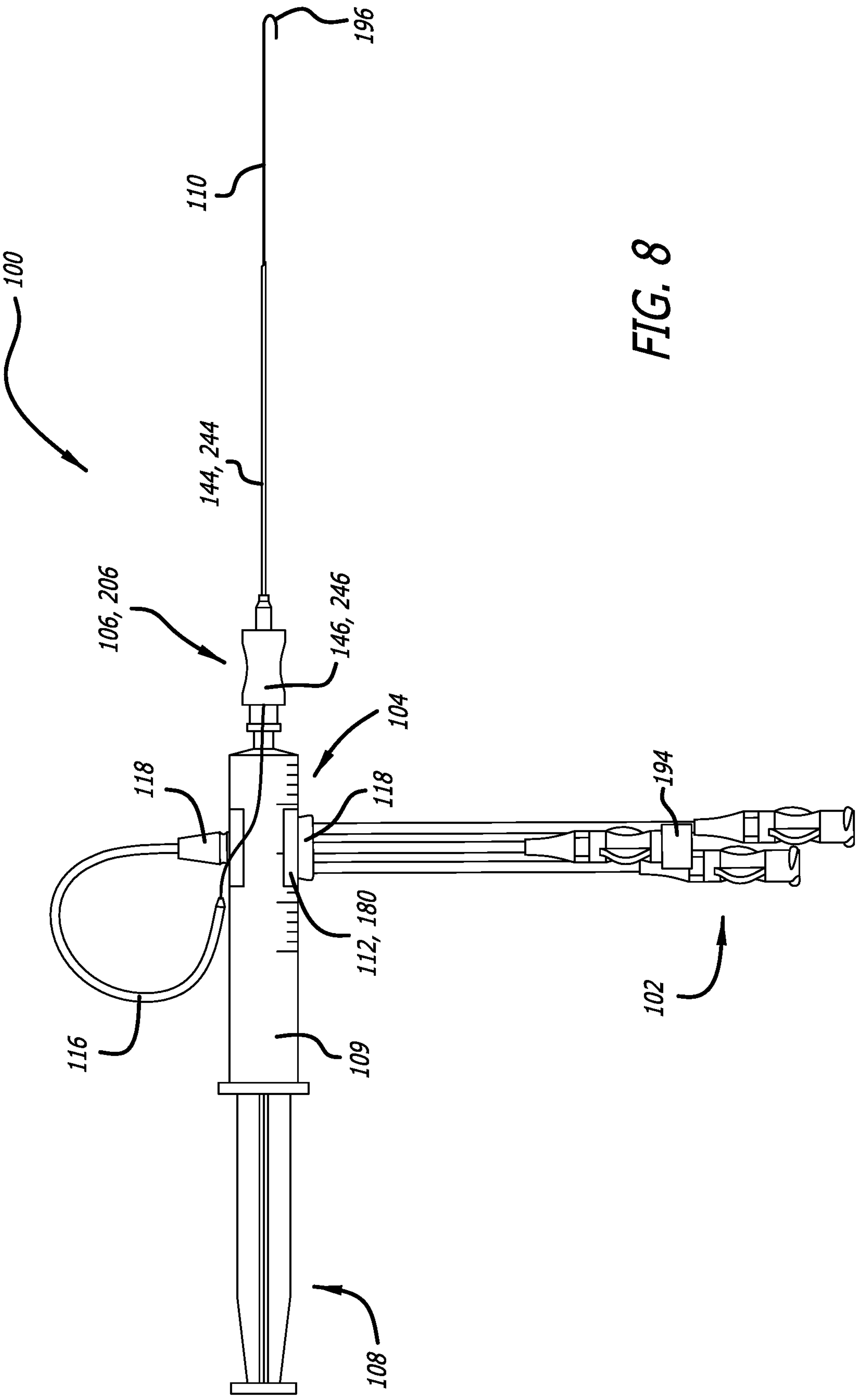
FIG. 8 illustrates the RICC insertion assembly of FIG. 7 in a deployed state thereof in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a catheter includes a portion or section of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal section, or the proximal length of the catheter can include the proximal end of the catheter; however, the proximal portion, the proximal section, or the proximal length of the catheter need not include the proximal end of the catheter. That is, unless context suggests otherwise, the proximal portion, the proximal section, or the proximal length of the catheter is not a terminal portion or terminal length of the catheter.

With respect to "distal," a "distal portion" or a "distal section" of, for example, a catheter includes a portion or section of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal section, or the distal length of the catheter can include the distal end of the catheter; however, the distal portion, the distal section, or the distal length of the catheter need not include the distal end of the catheter. That is, unless context suggests otherwise, the distal portion, the distal section, or the distal length of the catheter is not a terminal portion or terminal length of the catheter.

Unless defined otherwise, all technical and scientific terms used herein have the same meaning as commonly understood by those of ordinary skill in the art.

As set forth above with respect to the Seldinger technique, the number of steps can be time consuming, handling the number of medical devices can be awkward, and both of the foregoing can lead to patient trauma. In addition, there is a relatively high potential for touch contamination due to the number of medical devices that need to be interchanged during the Seldinger technique. Unfortunately, this is complicated by many of the foregoing medical devices being unwieldy elongate medical devices, which further increases the relatively high potential for touch contamination. As such, there is a need to reduce the number of steps and medical devices involved in introducing a catheter such as a CVC into a patient, as well as a need to reduce the unwieldiness of the foregoing medical devices.

Disclosed herein are compact RICC insertion assemblies and methods thereof that address at least the foregoing needs. For example, a RICC insertion assembly can include a RICC, an introducer assembly, an access guidewire, and a coupler coupling together the RICC and the introducer assembly. The RICC can include a catheter tube, a catheter hub, and one or more extension legs connected in the foregoing order. The introducer assembly can include an introducer needle coupled to a syringe. The introducer needle can include a needle-hub through hole passing through a needle hub and connecting to a needle-shaft lumen of a needle shaft. The access guidewire can include a proximal portion disposed in the RICC and a distal portion disposed in the needle-shaft lumen through the needle-hub through hole. The coupler can enforce a loop in the access guidewire over which the catheter tube follows, thereby compacting the RICC insertion assembly and making it easier to handle.

The foregoing features as well as other features of the RICC insertion assemblies and methods provided herein will become more apparent in view of the accompanying drawings and following description, which describe particular embodiments of the RICC insertion assemblies and methods in greater detail. However, it should be understood the RICCs of the RICC insertion assemblies are but one type of catheter that can be incorporated into catheter insertion assemblies like those provided herein. Indeed, peripherally inserted central catheters ("PICCs"), dialysis catheters, or the like can be modified in view of the RICCs and incorporated into respective catheter insertion assemblies for methods like those provided herein.

RICC Insertion Assemblies

FIGS. 1-19 illustrate a RICC insertion assembly 100 in accordance with some embodiments.

As shown, the RICC insertion assembly 100 can include a RICC 102, an introducer assembly 104 including an introducer needle 106 or 206 coupled to a syringe 108, an access guidewire 110, and a coupler 112 coupling together the RICC 102 and the introducer assembly 104, the RICC 102 and the access guidewire 110, or the introducer assembly 104 and the access guidewire 110. As set forth in more detail below, the proximal portion of the access guidewire 110 is disposed in the primary lumen 132 of the RICC 102 and the distal portion of the access guidewire 110 is disposed in the needle-shaft lumen 150 of the needle shaft 144 of the introducer needle 106 by way of the needle-hub through hole 154 through the needle hub 146 of the introducer needle 106. Alternatively, the distal portion of the access guidewire 110 is disposed in the needle lumen of the introducer needle 206. Depending upon the coupler 112, a loop 114 can be enforced in the access guidewire 110 over which the RICC 102, particularly the catheter tube 116 thereof, follows in at least the ready-to-deploy state of the RICC insertion assembly 100, thereby keeping the RICC insertion assembly 100 relatively compact and convenient to handle.

Notably, any component of the RICC insertion assembly 100 selected from at least the RICC 102, the introducer needle 104, the syringe 108, the access guidewire 110, and the coupler 112, or any portion of the component selected from the foregoing components, can include an antimicrobial thereon or therein. In an example, the catheter tube 116 of the RICC 102 can include an antimicrobial coating on an abluminal surface of the catheter tube 116, a luminal surface of the catheter tube 116, or both. In another example, a pre-extrusion material of the catheter tube 116 can include the antimicrobial admixed therein such that the antimicrobial is incorporated into the catheter tube 116 when extruded, the antimicrobial protecting both the abluminal surface of the catheter tube 116 and the luminal surface of the catheter tube 116 from microbial contamination.

FIGS. 25-29 illustrate the RICC 102 of the RICC insertion assembly 100 in accordance with some embodiments.

As shown, the RICC 102 includes a catheter tube 116, a catheter hub 118, one or more extension legs 120, and one or more extension-leg connectors 122.

FIGS. 26-29 illustrate various views of the catheter tube 116 of the RICC 102 in accordance with some embodiments.

The catheter tube 116 includes a first section 124 in a distal portion of the catheter tube 116, a second section 126 in the distal portion of the catheter tube 116 proximal of the first section 124, and a tapered junction 128 between the first and second sections 124 and 126 of the catheter tube 116.

Figure 29:
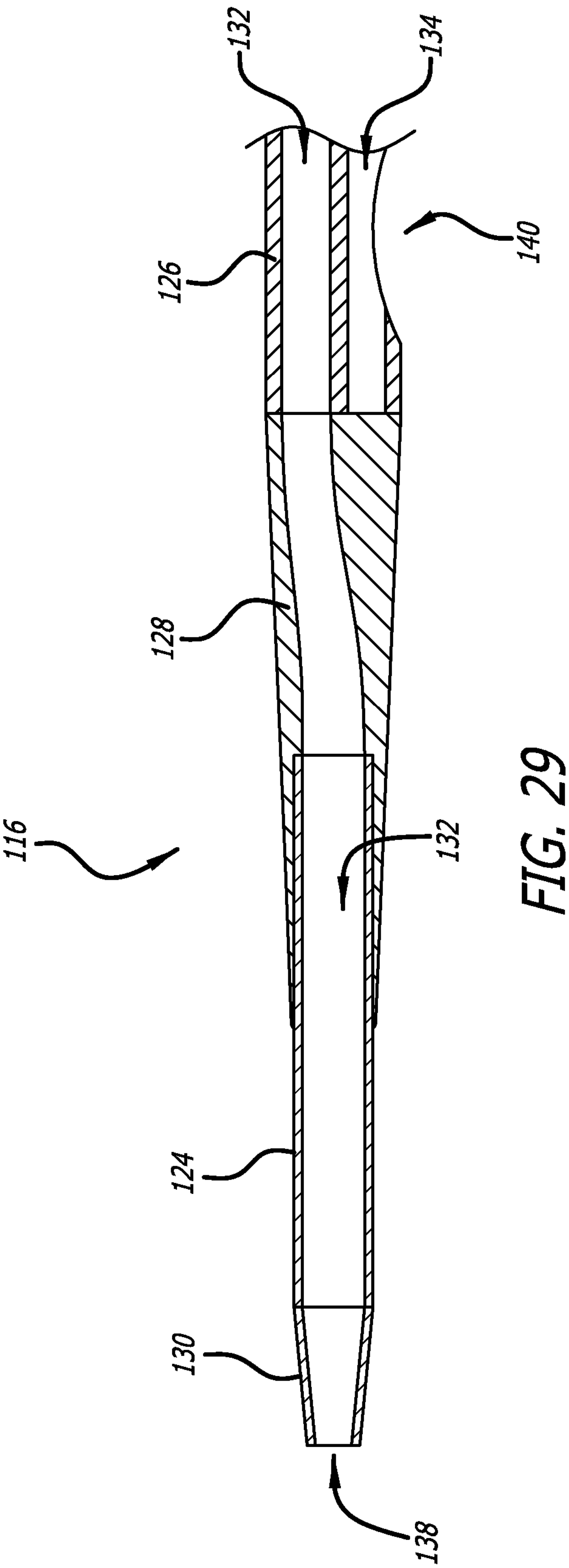
FIG. 29 illustrates a longitudinal cross section of the distal portion of the catheter tube in accordance with some embodiments.

The first section 124 of the catheter tube 116 includes a catheter tip 130 having a relatively short taper from an outer diameter of a distal portion of the first section 124 distal of the junction 128 to an outer diameter of a distal end of the first section 124. The taper of the catheter tip 130 is configured for immediate dilation of tissue about a needle tract established with the introducer needle 106 or 206 up to the outer diameter of the distal portion of the first section 124 of the catheter tube 116. As best shown in FIG. 29, the first section 124 of the catheter tube 116 also includes a proximal portion disposed in a bore of a distal portion of the junction 128 and fixedly coupled thereto such as by a solvent bond, an adhesive bond, or a heat weld.

The second section 126 of the catheter tube 116 includes a consistent outer diameter over its length from a distal end of the second section 126 to a proximal end of the second section 126. The consistent diameter of the second section 126 of the catheter tube 116 is configured for smooth insertion into the needle tract and targeted vasculature subsequent to any dilation by the first section 124 of the catheter tube 116 and the junction 128. The distal end of the second section 126 of the catheter tube 116 has a flat face flush with the flat-faced proximal end of the junction 128 and fixedly coupled thereto such as by a solvent bond, an adhesive bond, or a heat weld.

The junction 128 includes a taper over its length from a proximal end of the junction 128 to a distal end of the junction 128. The taper of the junction 128 is configured for immediate dilation of the tissue about the needle tract from the outer diameter of the proximal portion of the first section 124 of the catheter tube 116 to the outer diameter of the second section 126 of the catheter tube 116. An abluminal surface of the junction 128 smoothly transitions from an abluminal surface of the first section 124 of the catheter tube 116 to an abluminal surface of the second section 126 of the catheter tube 116 without edges that catch on skin when the catheter tube 116 is inserted into the needle tract. In addition to the edges being minimal to negligible, the edges can include solvent-interdiffused polymeric material of the polymeric materials from which the catheter tube 116 is formed, which smoothens the transitions from the first section 124 of the catheter tube 116 to the junction 128 and from the junction 128 to the second section 126 of the catheter tube 116. Notably, the junction 128 has a length approximately commensurate with a length of an exposed portion of the first section 124 of the catheter tube 116 or between lengths of exposed portions of the first and second sections 124 and 126 of the catheter tube 116. As such, the length of the exposed portion of the first section 124 of the catheter tube 116 is less than the length of the junction 128 up to approximately commensurate with the length of the junction 128.

The first section 124 of the catheter tube 116 is formed of a first polymeric material (e.g., a polytetrafluoroethylene, a polypropylene, or a polyurethane) having a first durometer. The second section 126 of the catheter tube 116 is formed of a second polymeric material (e.g., a polyvinyl chloride, a polyethylene, another polyurethane, or a silicone) having a second durometer less than the first durometer. For example, the first section 124 of the catheter tube 116 can be formed of a first polyurethane having the first durometer while the second section 126 of the catheter tube 116 can be formed of a second, different polyurethane (e.g., a same or different diisocyanate or triisocyanate reacted with a different diol or triol, a different diisocyanate or triisocyanate reacted with a same or different diol or triol, a same diisocyanate or triisocyanate reacted with a same diol or triol under different conditions or with different additives, etc.) having the second durometer less than the first durometer. Indeed, polyurethanes are advantageous for the catheter tube 116 in that polyurethanes can be relatively rigid at room-temperature but become more flexible in vivo at body temperature, which reduces irritation to vessel walls as well as phlebitis. Polyurethanes are also advantageous in that they can be less thrombogenic than some other polymers. The junction 128 is formed of the second polymeric material or a third polymeric material (e.g., yet another polyurethane) having a third durometer less than the first durometer and greater than, approximately equal to, or less than the second durometer.

It should be understood the first durometer of the first polymeric material, the second durometer of the second polymeric material, and the third durometer of the third polymeric material can be on different scales (e.g., Type A or Type D). With this understanding, the second durometer of the second polymeric material or the third durometer of the third polymeric material might not be numerically less than the first durometer of the first polymeric material when the second durometer or the third durometer is less than the first durometer. Indeed, the hardness of the second polymeric material or the third polymeric material can still be less than the hardness of the first polymeric material as the different scales—each of which ranges from 0 to 100—are designed for characterizing different materials in groups of the materials having a like hardness.

In accordance with the first section 124 of the catheter tube 116, the second section 126 of the catheter tube 116, and the junction 128 between the first and second sections 124 and 126 of the catheter tube 116 set forth above, the catheter tube 116 possesses a column strength sufficient to prevent buckling of the catheter tube 116 when inserted into a needle tract established with the introducer needle 106 or 206. The column strength of the catheter tube 116 is also sufficient to prevent buckling of the catheter tube 116 when advanced through a vasculature of a patient without dilation of tissue about the needle tract or any blood vessels of the vasculature beforehand with a separate dilator.

The catheter tube 116 includes one or more catheter-tube lumens extending through the catheter tube 116; however, only one catheter-tube lumen typically extends from a proximal end of the catheter tube 116 to a distal end of the catheter tube 116 in a multiluminal RICC (e.g., a diluminal RICC, a triluminal RICC, a tetraluminal RICC, a pentaluminal RICC, a hexaluminal RICC, etc.). Indeed, the first section 124 of the catheter tube 116 typically includes a single lumen therethrough as shown in FIG. 29.

The catheter hub 118 is coupled to a proximal portion of the catheter tube 116. The catheter hub 118 includes one or more catheter-hub lumens corresponding in number to the one-or-more catheter-tube lumens. The one-or-more catheter-hub lumens extends through an entirety of the catheter hub 118 from a proximal end of the catheter hub 118 to a distal end of the catheter hub 118.

Each extension leg of the one-or-more extension legs 120 is coupled to the catheter hub 118 by a distal portion thereof. The one-or-more extension legs 120 respectively include one or more extension-leg lumens, which, in turn, correspond in number to the one-or-more catheter-hub lumens. Each extension-leg lumen of the one-or-more extension-leg lumens extends through an entirety of the extension leg from a proximal end of the extension leg to a distal end of the extension leg.

Each extension-leg connector of the one-or-more extension-leg connectors 122 is over a proximal portion of an extension leg of the one-or-more extension legs 120. For example, each extension-leg connector of the one-or-more extension-leg connectors 122 can be a Luer connector over a proximal portion of an extension leg of the one-or-more extension legs 120. Through such an extension-leg connector, a corresponding extension leg and the extension-leg lumen thereof can be connected to another medical device and a lumen thereof. However, in the ready-to-deploy state of the RICC insertion assembly 100 of FIGS. 10 and 11 at least one extension-leg connector (e.g., the extension-leg connector including part of the primary lumen 132 of the RICC 102) is connected to the access-guidewire hub 194, which, in turn, is coupled to the needle hub 146 or 246 of the introducer needle 106 or 206. The access-guidewire hub 194 thusly also functions as the coupler 112 coupling together the RICC 102 and the introducer assembly 104 to enforce the loop 114 in both the access guidewire 110 and the RICC 102 thereover.

As shown, the RICC 102 is a triluminal RICC including a set of three lumens; however, the RICC 102 is not limited to the set of the three lumens as set forth above. The set of three lumens includes a primary lumen 132, a secondary lumen 134, and a tertiary lumen 136 formed of fluidly connected portions of three catheter-tube lumens, three catheter-hub lumens, and three extension-leg lumens. The primary lumen 132 has a primary-lumen aperture 138 in the distal end of the first section 124 of the catheter tube 116, which corresponds to the distal end of the catheter tube 116 and a distal end of the RICC 102. The secondary lumen 134 has a secondary-lumen aperture 140 in a side of the distal portion of the catheter tube 116. The tertiary lumen 136 has a tertiary-lumen aperture 142 in the side of the distal portion of the catheter tube 116 proximal of the secondary-lumen aperture 140.

Figure 20:
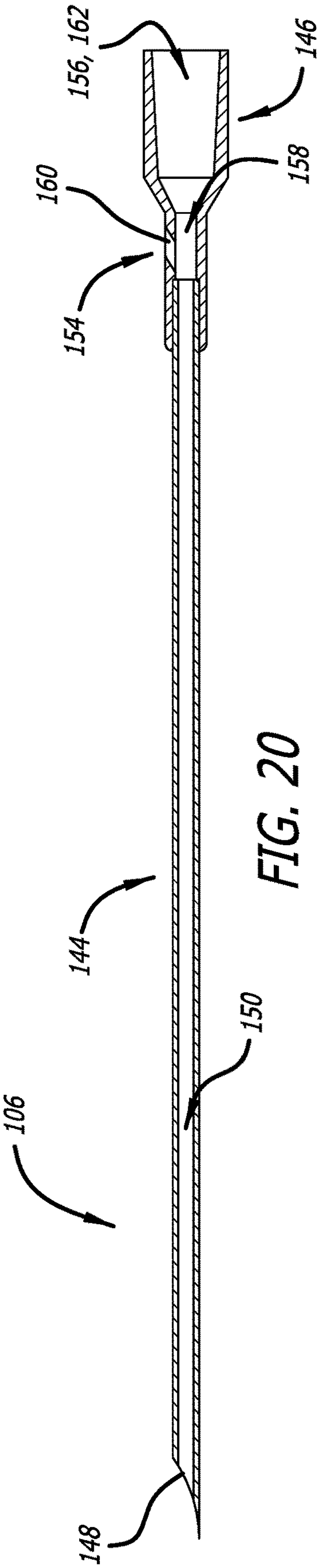
FIG. 20 illustrates a longitudinal cross section of the introducer needle in accordance with some embodiments.
Figure 21:
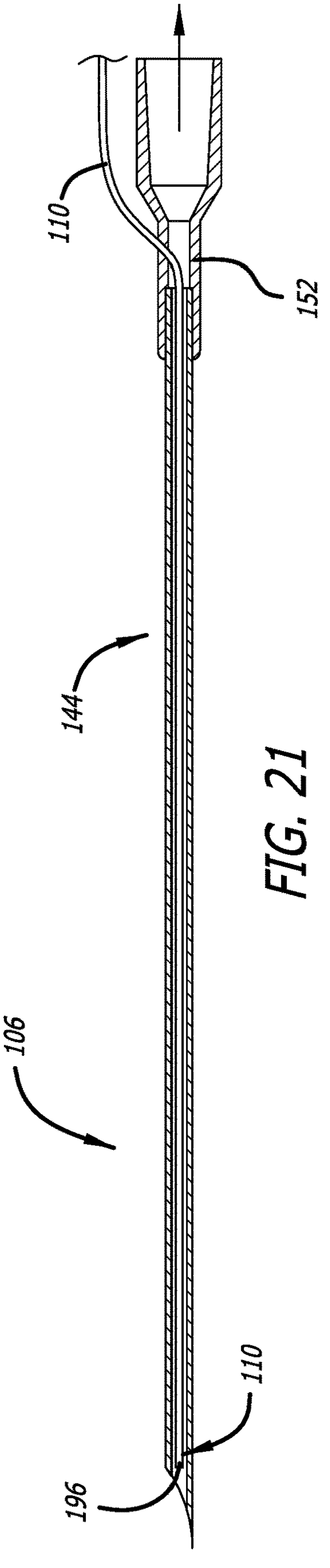
FIG. 21 illustrates a longitudinal cross section of the introducer needle with the access guidewire disposed therein in a ready-to-deploy state thereof in accordance with some embodiments.

FIGS. 20 and 21 illustrate various views of the introducer needle 106 of the RICC insertion assembly 100 in accordance with some embodiments.

As shown, the introducer needle 106 includes a needle shaft 144 and a needle hub 146 over a proximal portion of the needle shaft 144. The introducer needle 106 further includes a needle lumen formed of fluidly connected portions of the needle-shaft lumen 150 and the needle-hub lumen 158 set forth below.

The needle shaft 144 includes a needle tip 148 in a distal portion of the needle shaft 144 and a needle-shaft lumen 150 extending from a proximal end of the needle shaft 144 through the needle tip 148.

The needle tip 148 includes a bevel having the tip bevel 168 and the primary bevel 170 proximal of the tip bevel 168 set forth below with respect to the needle tip 248 of the needle shaft 244 of the introducer needle 206. A tip-bevel angle of the tip bevel 168 is greater than a primary-bevel angle of the primary bevel 170 such that the bevel provides a smooth transition over the needle tip 148. Such a needle tip is thusly configured for establishing a needle tract from an area of skin into a blood-vessel lumen of a patient in accordance with the needle tract-establishing step of the method set forth below.

The needle-shaft lumen 150 is configured to accommodate the access guidewire 110 therein during at least the needle tract-establishing step and the blood-aspirating step of the method set forth below. Indeed, an annular space between an inner diameter of the needle shaft 144 and an outer diameter of the access guidewire 110 is sufficiently narrow so as to prevent the access guidewire 110 from kinking but sufficiently wide so as to allow blood flashback or blood aspiration therethrough.

The needle hub 146 includes a neck 152 or needle-connecting portion in a distal portion of the needle hub 146, a needle-hub through hole 154, and a needle-hub connector 156 in a proximal portion of the needle hub 146. The needle hub 146 further includes a needle-hub lumen 158 formed between the neck 152 and the needle-hub connector 156, particularly that not occupied by the proximal portion of the needle shaft 144 or the syringe tip when disposed in the needle-hub connector 156.

The needle-hub through hole 154 passes through a side of the needle hub 146 such as the neck 152 and connects to the needle-shaft lumen 150 by way of the proximal end of the needle shaft 144, optionally through an intervening portion of the needle-hub lumen 158. Being that the needle-hub through hole 154 has an inner diameter commensurate with that of the needle-shaft lumen 150, the access guidewire 110 can be passed through the needle-hub through hole 154 and into the needle-shaft lumen 150. The needle-hub through hole 154 can include a gasket 160 disposed therein. Such a gasket is configured to seal around the access guidewire 110 and allow a vacuum to be drawn with the syringe 108 without leaking through the needle-hub through hole 154. The gasket 160 can be a septum or one or more 'O'-rings, but the gasket 160 is not limited thereto.

The needle-hub connector 156 includes a needle-hub bore 162 and an optional needle-hub flange (not shown) about the needle-hub connector 156.

The needle-hub bore 162 of the needle-hub connector 156 is configured to accept a syringe tip of the syringe 108 therein for fluidly connecting the introducer needle 106 to the syringe 108. Indeed, the needle-hub bore 162 can have a Luer taper (e.g., a 6% taper) configured to accept the syringe tip therein, which syringe tip can be complementarily configured with a Luer taper.

When present, the needle-hub flange of the needle-hub connector 156 is configured to screw together with internal threads of a threaded collar around the syringe tip of the syringe 108. While the threaded collar of the syringe 108 is also optional, the needle-hub flange advantageously provides a so-called Luer lock-style connection with the internal threads of the threaded collar when both are present. This provides added security against inadvertent disconnection of the introducer needle 106 and the syringe 108 over that provided by an otherwise Luer slip-style connection.

Figures 22, 23, 24:
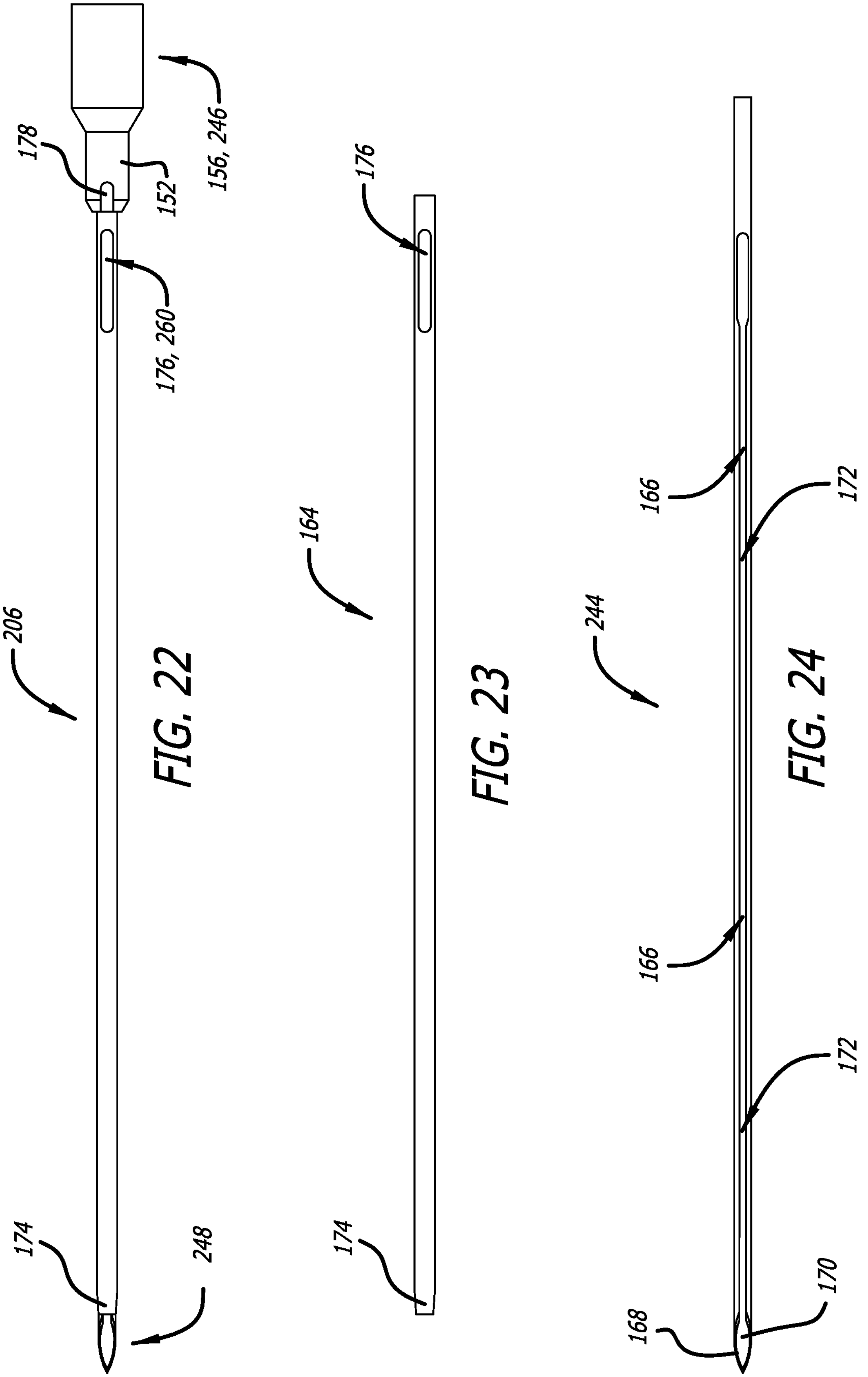
FIG. 22 illustrates the introducer needle in accordance with some embodiments.
FIG. 23 illustrates a sheath of the introducer needle in accordance with some embodiments.
FIG. 24 illustrates a needle shaft of the introducer needle in accordance with some embodiments.
Figure 25:
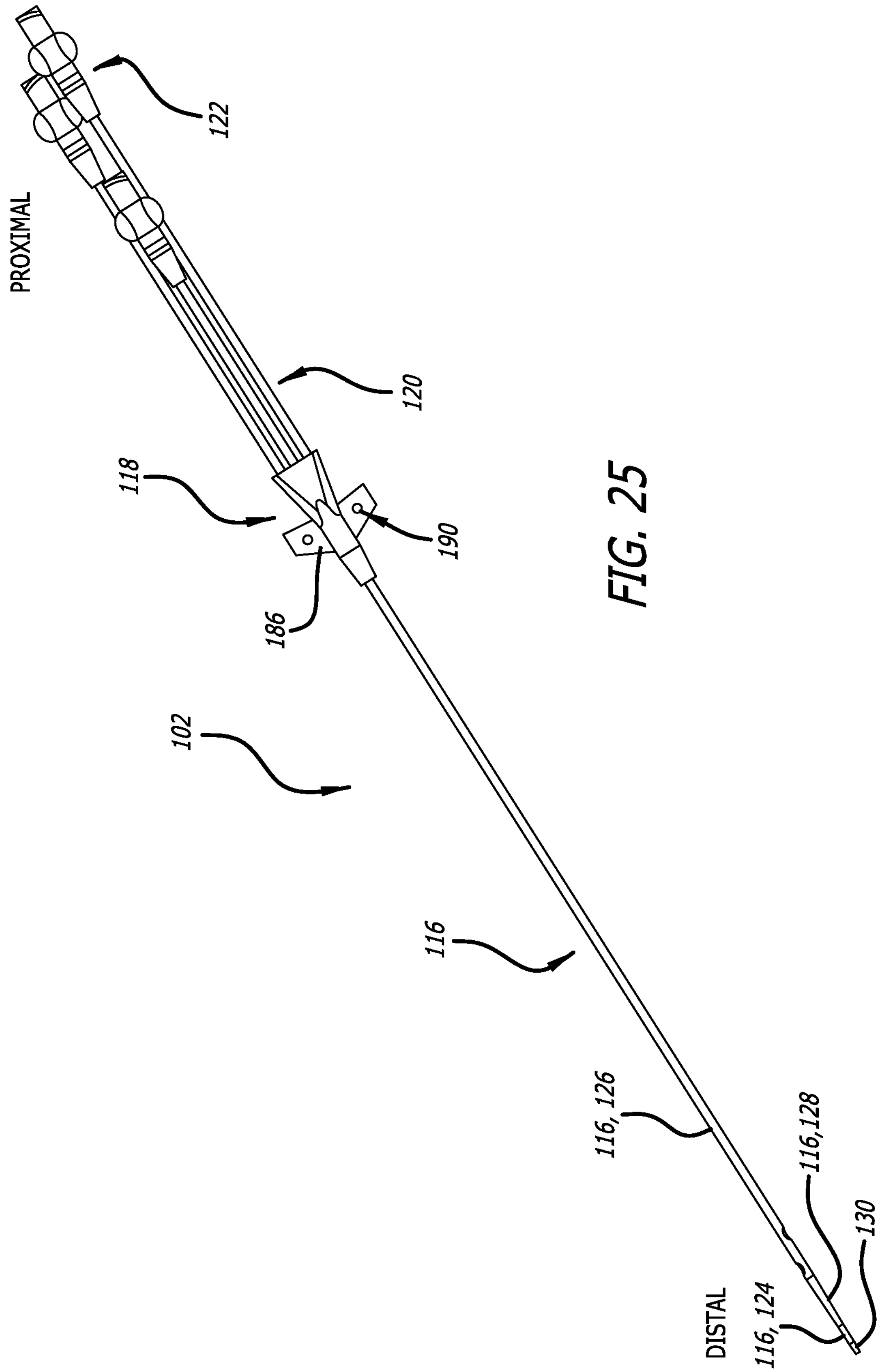
FIG. 25 illustrates the RICC in accordance with some embodiments.

FIGS. 22-24 illustrate various views of the introducer needle 206 of the RICC insertion assembly 100 in accordance with some embodiments.

As shown, the introducer needle 206 includes a needle shaft 244, a sheath 164 over the needle shaft 244, and a needle hub 246 over both a proximal portion of the needle shaft 244 and a proximal portion of the sheath 164.

The needle shaft 244 includes a needle tip 248 in a distal portion of the needle shaft 244 and a longitudinal needle slot 166 extending from the proximal portion of the needle shaft 244 through the needle tip 248.

The needle tip 248 includes a bevel having a tip bevel 168 and a primary bevel 170 proximal of the tip bevel 168. A tip-bevel angle of the tip bevel 168 is greater than a primary-bevel angle of the primary bevel 170 such that the bevel provides a smooth transition over the needle tip 248. Such a needle tip is thusly configured for establishing a needle tract from an area of skin into a blood-vessel lumen of a patient in accordance with the needle tract-establishing step of the method set forth below.

The needle slot 166 extends from the proximal portion of the needle shaft 244 through the needle tip 248, thereby forming a needle channel 172 along a majority of a length of the needle shaft 244 as opposed to a needle lumen therethrough. The needle slot 166 has a width sized in accordance with the outer diameter of the access guidewire 110, which allows the access guidewire 110 to pass from the proximal portion of the needle shaft 244 through the needle tip 248 when the introducer needle-withdrawing step of the method set forth below is performed.

While the needle shaft 244 includes the foregoing needle slot 166, it should be understood the introducer needle 206 includes a needle lumen; however, the needle lumen results from the combination of the needle shaft 244 and the sheath 164 over the needle shaft 244. Indeed, the sheath 164 over the needle shaft 244 seals the needle slot 166 thereunder forming the needle lumen of the introducer needle 206 and enabling the syringe 108 to aspirate blood in accordance with the blood-aspirating step of the method set forth below.

The sheath 164 includes a sheath tip 174 in a distal portion of the sheath 164 and a sheath opening 176 in a side of the proximal portion of the sheath 164.

The sheath tip 174 includes a relatively short taper from an outer diameter of the distal portion of the sheath 164 to an outer diameter of a distal end of the sheath 164, the latter of which is commensurate with an outer diameter of the distal portion of the needle shaft 244. The taper has a taper angle less than the primary-bevel angle of the primary bevel 170 of the needle tip 248, which, in turn, is less than the tip-bevel angle of the tip bevel 168 of the needle tip 248. The sheath tip 174 including such a taper is configured to provide a smooth transition from the needle tip 248 to a sheath body proximal of the sheath tip 174 for the needle tract-establishing step of the method set forth below.

The sheath opening 176 opens to the needle slot 166 of the needle shaft 244 allowing the access guidewire 110 to pass through the sheath opening 176 and into the needle slot 166 in the ready-to-deploy state of the RICC insertion assembly 100. Thus, the sheath opening 176 has a width approximately commensurate with a width of the needle slot 166, which, in turn, is sized in accordance with the outer diameter of the access guidewire 110. The sheath opening 176 also has a length sufficient to allow the access guidewire 110 to pass through the sheath opening 176 and into the needle slot 166 while also accommodating a blade of a clinician's choice (e.g., a scalpel blade) under a distal end of the sheath opening 176. Notably, the sheath 164 over the needle shaft 244 seals the needle slot 166 thereunder except for that under the sheath opening 176. However, like the needle-hub through hole 154 of the introducer needle 106, the sheath opening 176 can include a gasket 260 disposed therein sealing the proximal portions of the needle shaft 244 and the sheath 164 therein, thereby enabling the syringe 108 to aspirate blood in accordance with the blood-aspirating step of the method set forth below.

The sheath 164, or a sheath body thereof, is formed of a polymeric material configured to facilitate a smooth, consistent insertion of the introducer needle 206 from an area of skin to a blood-vessel lumen of a patient in accordance with the needle tract-establishing step of the method set forth below. In addition, the polymeric material has mechanical properties at a thickness of the sheath 164 sufficient to withstand collapse of the sheath 164 into the needle slot 166 of the needle shaft 244 when the blood-aspirating step of the method set forth below is performed, notably, while also facilitating cutting at least a portion of the sheath 164 off the needle shaft 244. Such a polymeric material can include, but is not limited to, polyethylene, polypropylene, or polytetrafluoroethylene.

The needle hub 246 includes an access-guidewire channel 178 in a distal portion of the needle hub 246 and the needle-hub connector 156 in a proximal portion of the needle hub 246.

The access-guidewire channel 178 of the needle hub 246 is configured to allow the access guidewire 110 to pass over the needle hub 246 and direct the access guidewire 110 into the sheath opening 176. The access-guidewire channel 178 is open such that the access guidewire 110 lies in the access-guidewire channel 178 in at least the ready-to-deploy state of the RICC insertion assembly 100. Advantageously, the open access-guidewire channel 178 allows the access guidewire 110 to remain in place when the introducer needle 206 is withdrawn from the RICC insertion assembly 100 in accordance with the introducer needle-withdrawing step of the method set forth below.

As set forth above, the needle-hub connector 156 includes the needle-hub bore 162 and an optional needle-hub flange (not shown) about the needle-hub connector 156.

The needle-hub bore 162 of the needle-hub connector 156 is configured to accept the syringe tip of the syringe 108 therein for fluidly connecting the introducer needle 206 to the syringe 108. Indeed, the needle-hub bore 162 can have a Luer taper (e.g., a 6% taper) configured to accept the syringe tip therein, which syringe tip can be complementarily configured with a Luer taper.

When present, the needle-hub flange of the needle-hub connector 156 is configured to screw together with the internal threads of the threaded collar around the syringe tip of the syringe 108. While the threaded collar of the syringe 108 is also optional, the needle-hub flange advantageously provides the so-called Luer lock-style connection with the internal threads of the threaded collar when both are present. This provides added security against inadvertent disconnection of the introducer needle 206 and the syringe 108 over that provided by the otherwise Luer slip-style connection.

FIGS. 1-9 illustrate various view of the coupler 112 coupling together the RICC 102 and the introducer assembly 104 by way of the catheter hub 118 in accordance with some embodiments.

As shown, the coupler 112 coupling together the RICC 102 and the introducer assembly 104 can be a separate coupler including either a barrel clip 180 or a needle-hub clip 182 with a catheter-hub seat 184 opposite the clip 180 or 182. The coupler 112 being a separate coupler enables the catheter hub 118 to be decoupled from the coupler 112, thereby making suture wings 186 of the catheter hub 118 available for securing (via suturing) the catheter hub 118 to a patient upon placing the RICC 102 in the patient's vasculature.

Figure 9:
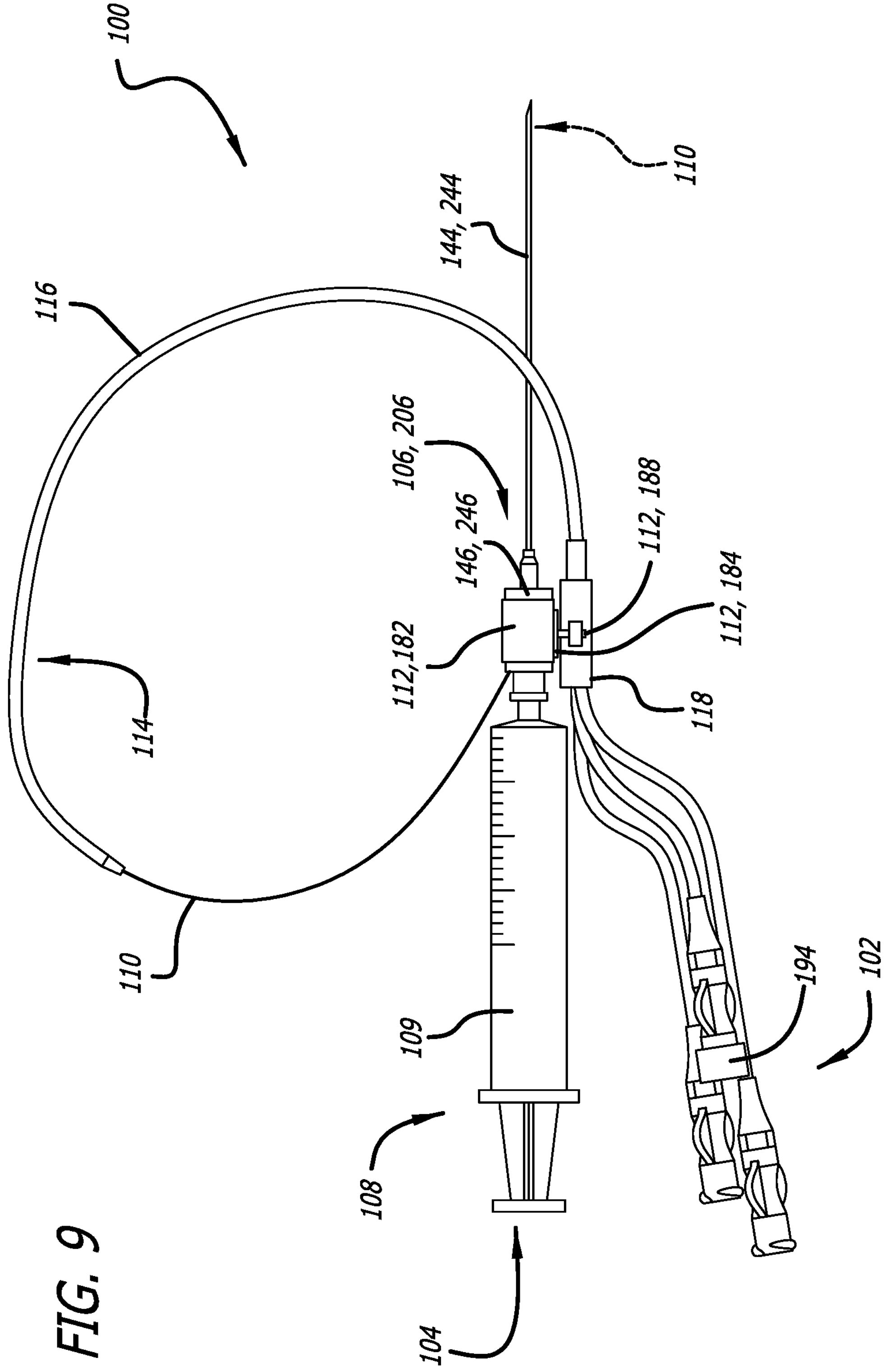
FIG. 9 illustrates the RICC insertion assembly in a ready-to-deploy state thereof with a second coupler coupling together the catheter hub of the RICC and a needle hub of an introducer needle of the introducer assembly to enforce a loop in the access guidewire of a fifth configuration in accordance with some embodiments.

The barrel clip 180 can be a Terry-type clip extending from the coupler 112 configured to firmly, but slidably, clip onto a barrel 109 of the syringe 108 as shown in FIGS. 1-8. The needle-hub clip 182, too, can be a Terry-type clip extending from the coupler 112 configured to clip onto the needle hub 146 or 246 of the introducer needle 106 or 206 as shown in FIG. 9.

Whether the coupler 112 includes the barrel clip 180 or the needle-hub clip 182, the catheter-hub seat 184 of the coupler 112 is configured to seat the catheter hub 118 thereon. Notably, the catheter-hub seat 184 can include posts 188 extending therefrom as shown in at least FIGS. 3-6 and 9. The posts 188 are configured to insert into suture-wing holes 190 of the suture wings 186 extending from the catheter hub 118 to secure the catheter hub 118 on the catheter-hub seat 184.

The clip 180 or 182 and the catheter-hub seat 184 of the coupler 112 can be fixed or rotatable with respect to each other. When the clip 180 or 182 and the catheter-hub seat 184 of the coupler 112 are fixed with respect to each other, the coupler 112 typically orients the catheter hub 118 in either a longitudinal or transverse orientation with respect to a central axis of the introducer assembly 104, which, in turn, orients the catheter hub 118 in either a longitudinal or transverse orientation with respect to the barrel 109 of the syringe 108 or the needle hub 146 or 246. That said, such a coupler need not orient the catheter hub 118 in the longitudinal or transverse orientation with respect to the central axis of the introducer assembly 104. Indeed, the clip 180 or 182 and the catheter-hub seat 184 of the coupler 112 can be fixed with respect to each other to orient the catheter hub 118 in any suitable orientation with respect to the central axis of the introducer assembly 104. However, to provide clinicians options for implementing their preferred orientations of the catheter hub 118 to the central axis of the introducer assembly 104, the clip 180 or 182 and the catheter-hub seat 184 can include a Hirth-like joint therebetween, thereby making the clip 180 or 182 and the catheter-hub seat 184 rotatable with respect to each other. Such a coupler allows a clinician to orient the catheter hub 118 in any clinician-desired orientation thereof with respect to the central axis of the introducer assembly 104, which orientation might need to be changed depending upon procedural or environmental circumstances. Notably, reorienting the catheter hub 118 with respect to the central axis of the introducer assembly 104 can reorient the loop 114 of the access guidewire 110 and the catheter hub 118 thereover.

Figure 10:
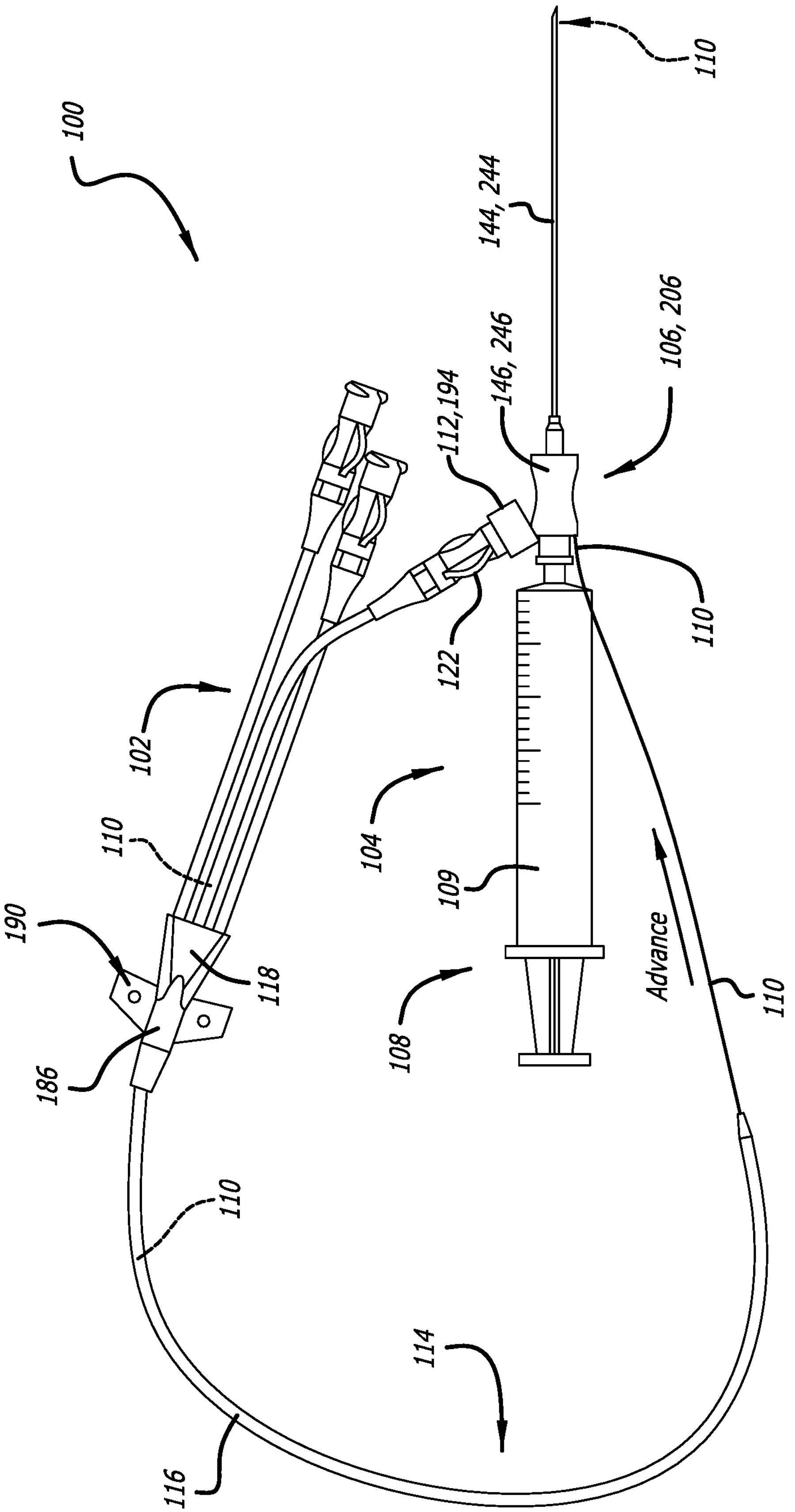
FIG. 10 illustrates the RICC insertion assembly in a ready-to-deploy state thereof with a third coupler coupling together an extension-leg connector of an extension leg of the RICC and the needle hub of the introducer needle of the introducer assembly to enforce a loop in the access guidewire of a sixth configuration in accordance with some embodiments.
Figure 11:
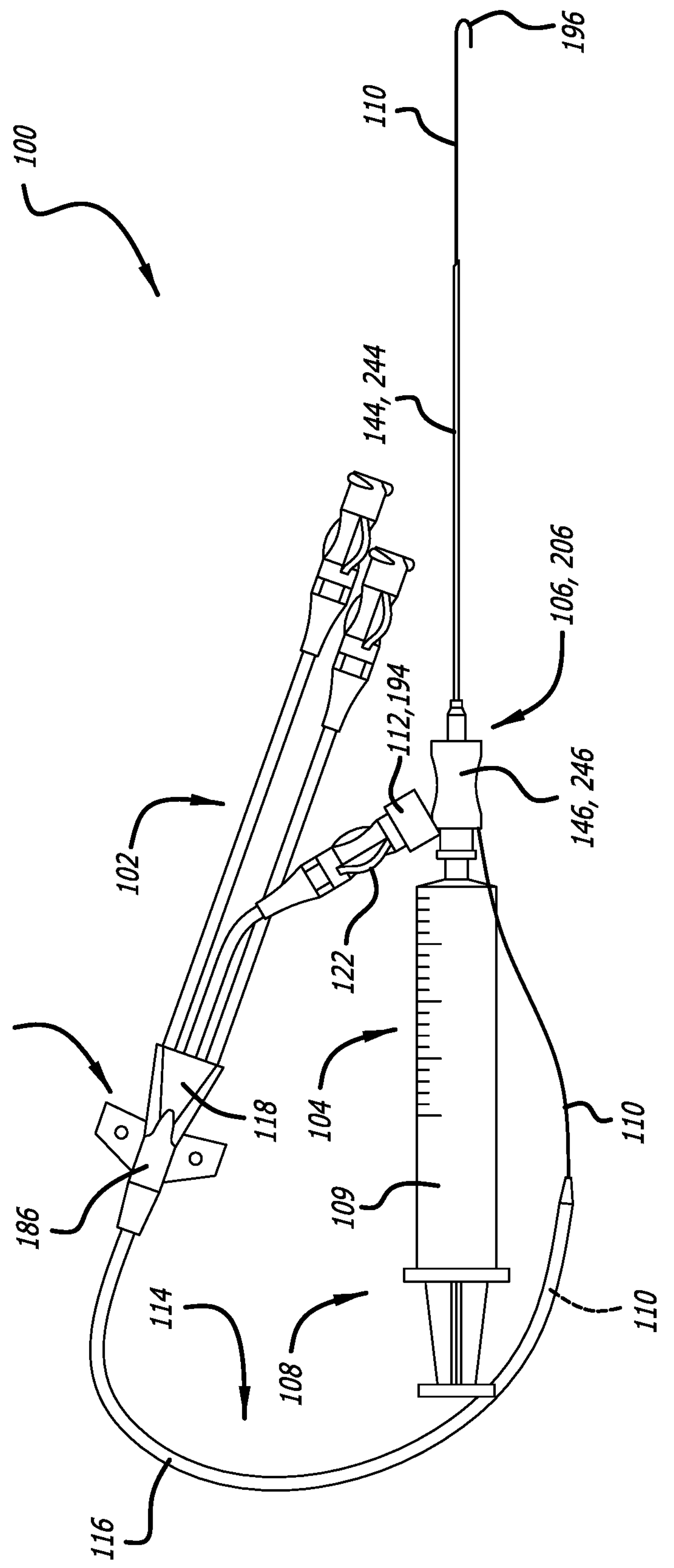
FIG. 11 illustrates the RICC insertion assembly of FIG. 10 in a deployed state thereof in accordance with some embodiments.

FIGS. 10 and 11 illustrate various view of the coupler 112 coupling together the RICC 102 and the introducer assembly 104 by way of the access-guidewire hub 194 in accordance with some embodiments.

As shown, the coupler 112 coupling together the RICC 102 and the introducer assembly 104 can be an integrated coupler such as a portion of the access-guidewire hub 194. As set forth below, the proximal end of the access guidewire 110 is coupled to the access-guidewire hub 194. In addition, the access-guidewire hub 194 can be configured to screw onto an extension-leg connector extending from the proximal portion of an extension leg of the one-or-more extension legs 120. When the coupler 112 is configured as an integrated coupler, a proximal end of the access-guidewire hub 194 is configured to couple to another side of the needle hub 146 or 246 opposite that including the needle-hub through hole 154 or the sheath opening 176. Advantageously, when the coupler 112 is the foregoing portion of the access-guidewire hub 194, it does not interfere with the catheter hub 118 in any way, thereby keeping the catheter hub 118 available for securing the catheter hub 118 to a patient upon placing the RICC 102 in the patient's vasculature.

Notably, portions of the RICC 102 other than the catheter hub 118 and the one-or-more extension legs 120 can be coupled to the introducer assembly 104, optionally, in combination with the catheter hub 118 or the one-or-more extension legs 120, to further place the RICC insertion assembly 100 in a compact form. Indeed, any of a number of portions of the RICC 102 can be coupled to the introducer assembly 104 to enforce the loop 114 in the access guidewire 110 over which the catheter tube 116 follows. By enforcing the loop 114 in the access guidewire 110 and the catheter tube 116, the coupler 112 compacts the RICC insertion assembly 100 making it easier to handle, thereby reducing the likelihood of touch contamination.

Figure 12:
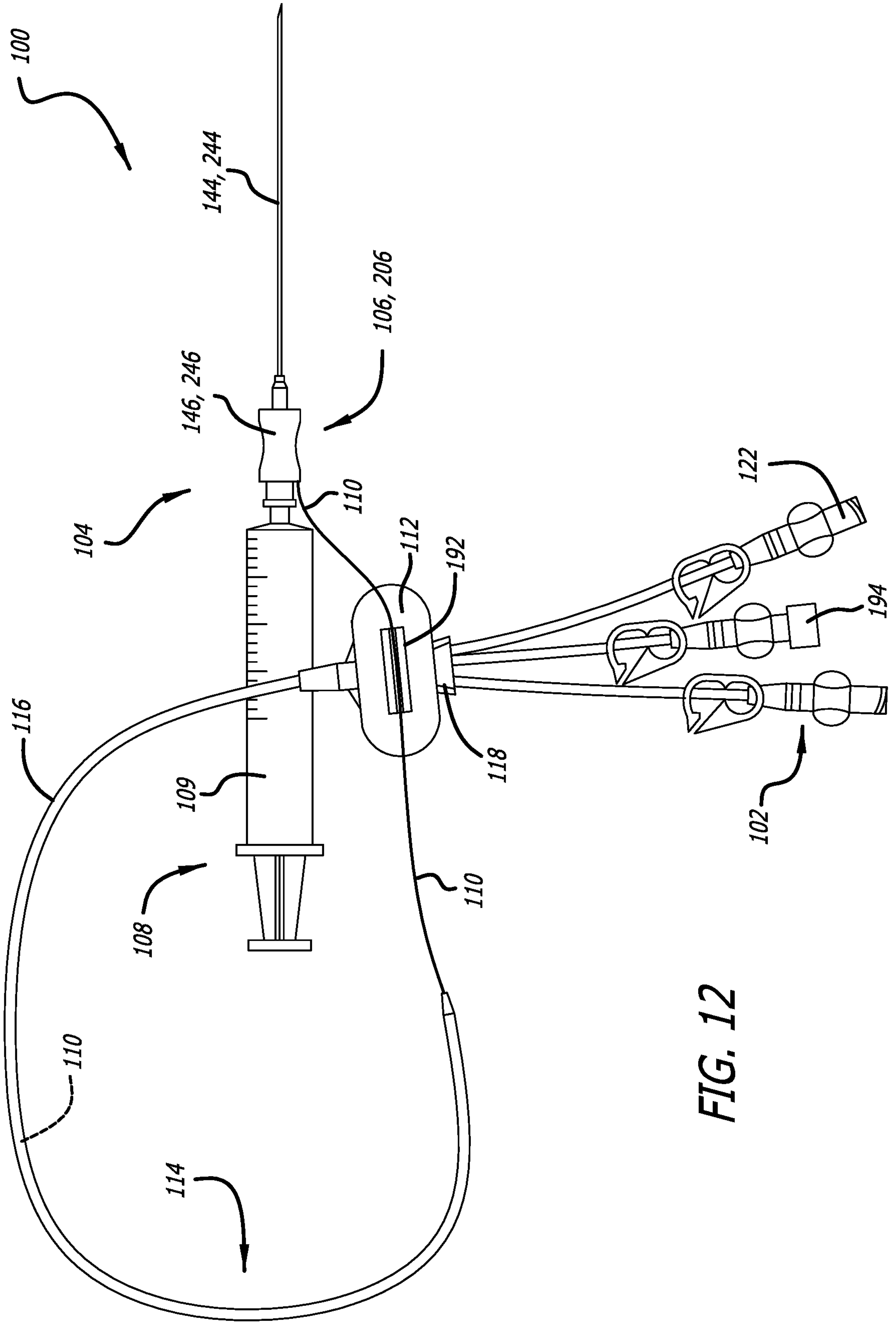
FIG. 12 illustrates the RICC insertion assembly in a ready-to-deploy state thereof with a fourth coupler coupling together the catheter hub of the RICC and the access guidewire to enforce a loop in the access guidewire of a seventh configuration in accordance with some embodiments.
Figure 13:
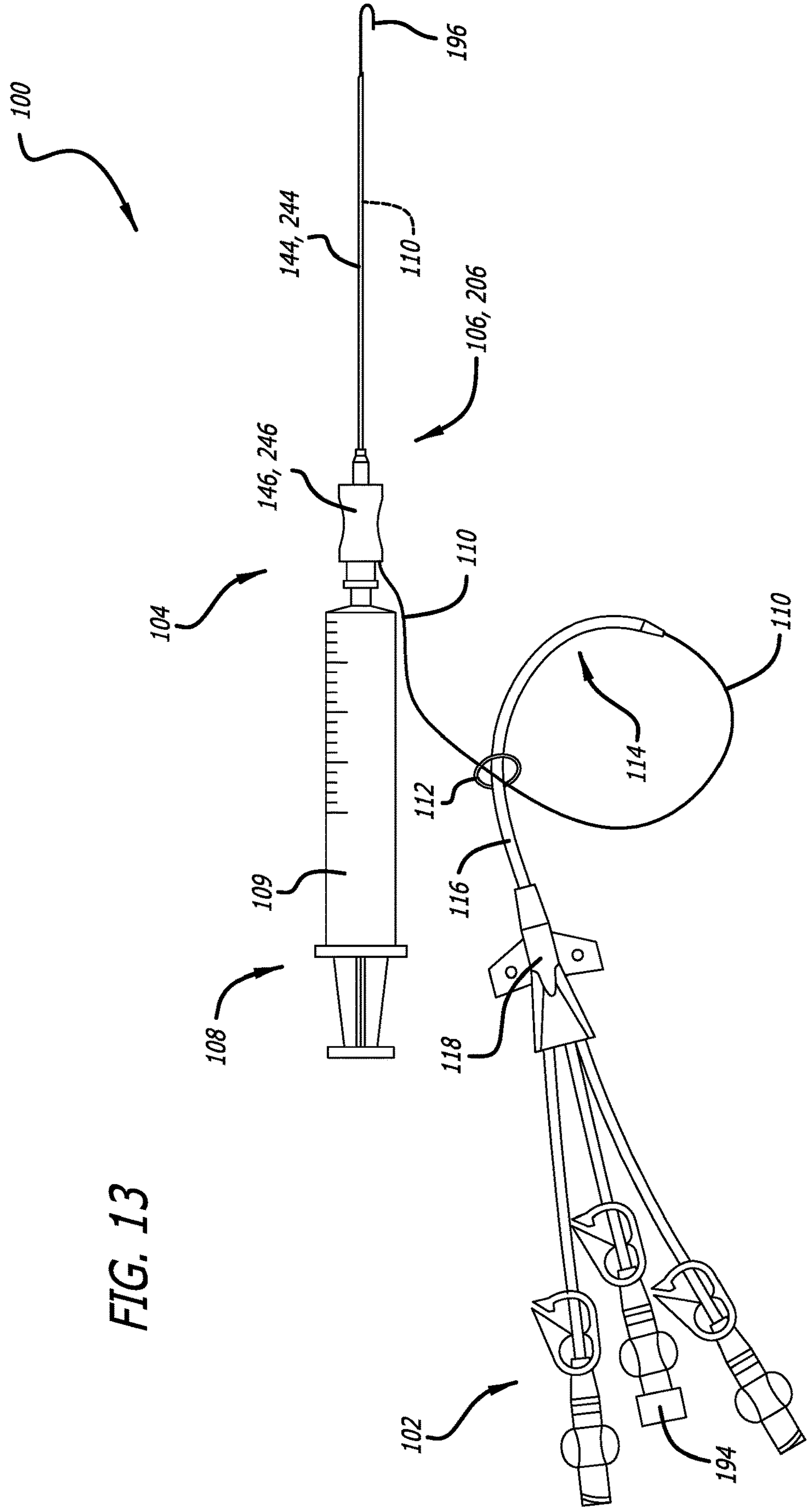
FIG. 13 illustrates the RICC insertion assembly with a fifth coupler coupling together the catheter tube of the RICC and the access guidewire to enforce a loop in the access guidewire of an eighth configuration in accordance with some embodiments.
Figure 14:
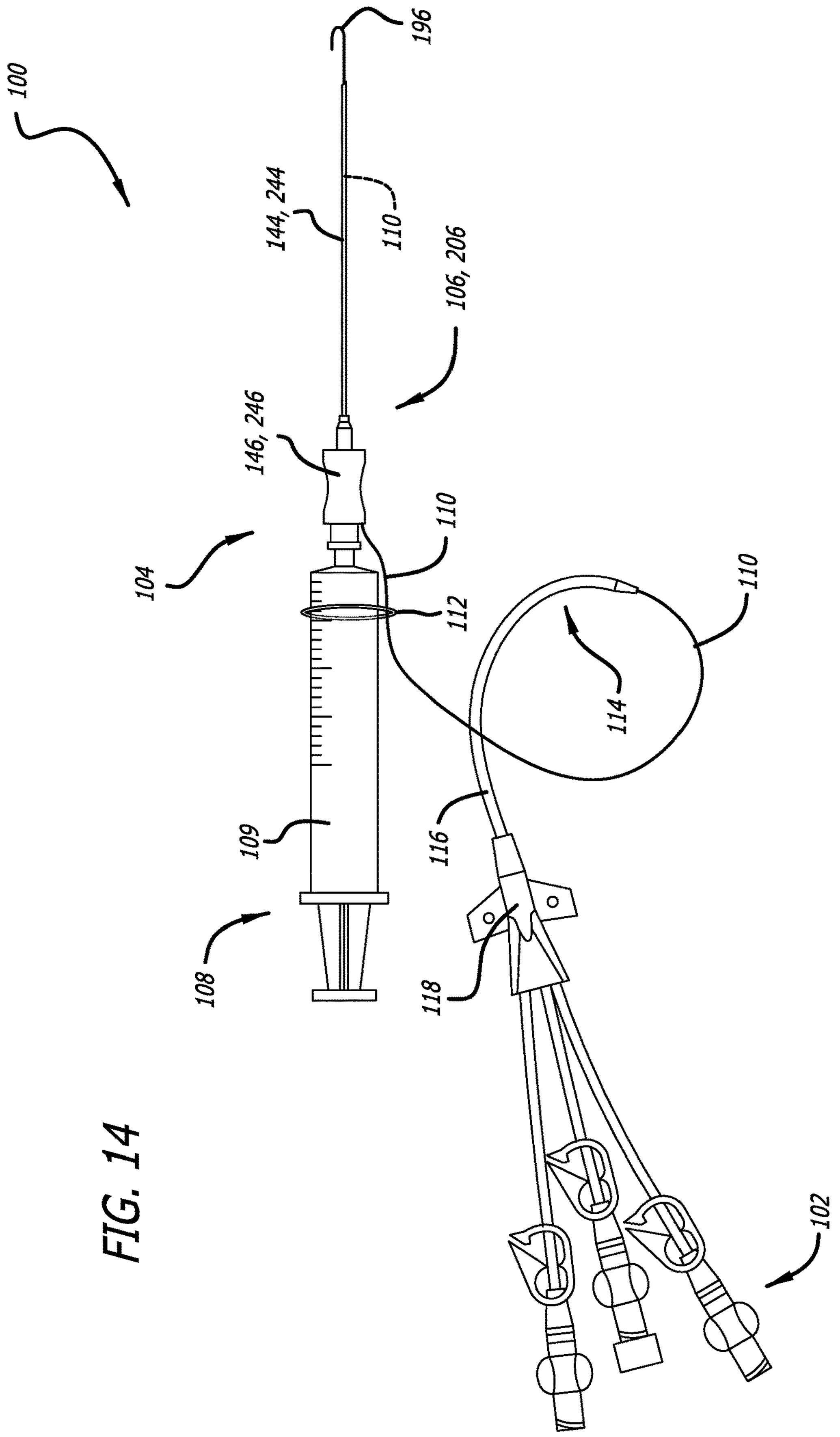
FIG. 14 illustrates the RICC insertion assembly with a sixth coupler coupling together the barrel of the syringe of the introducer assembly and the access guidewire in accordance with some embodiments.
Figure 15:
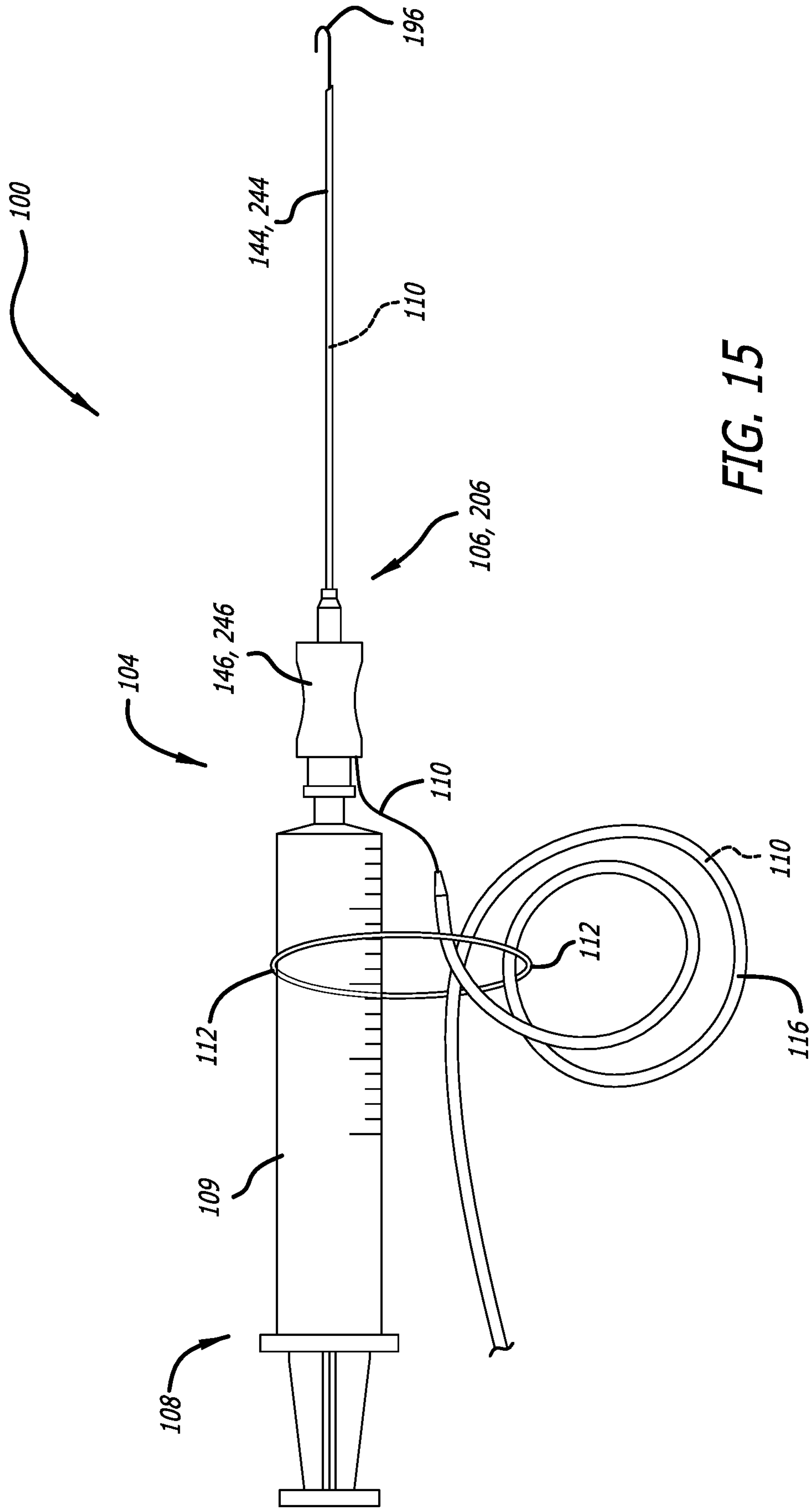
FIG. 15 illustrates the RICC insertion assembly with a seventh coupler coupling together the catheter tube of the RICC and the barrel of the syringe of the introducer assembly to enforce a number of loops in the catheter tube of a first configuration in accordance with some embodiments.
Figure 16:
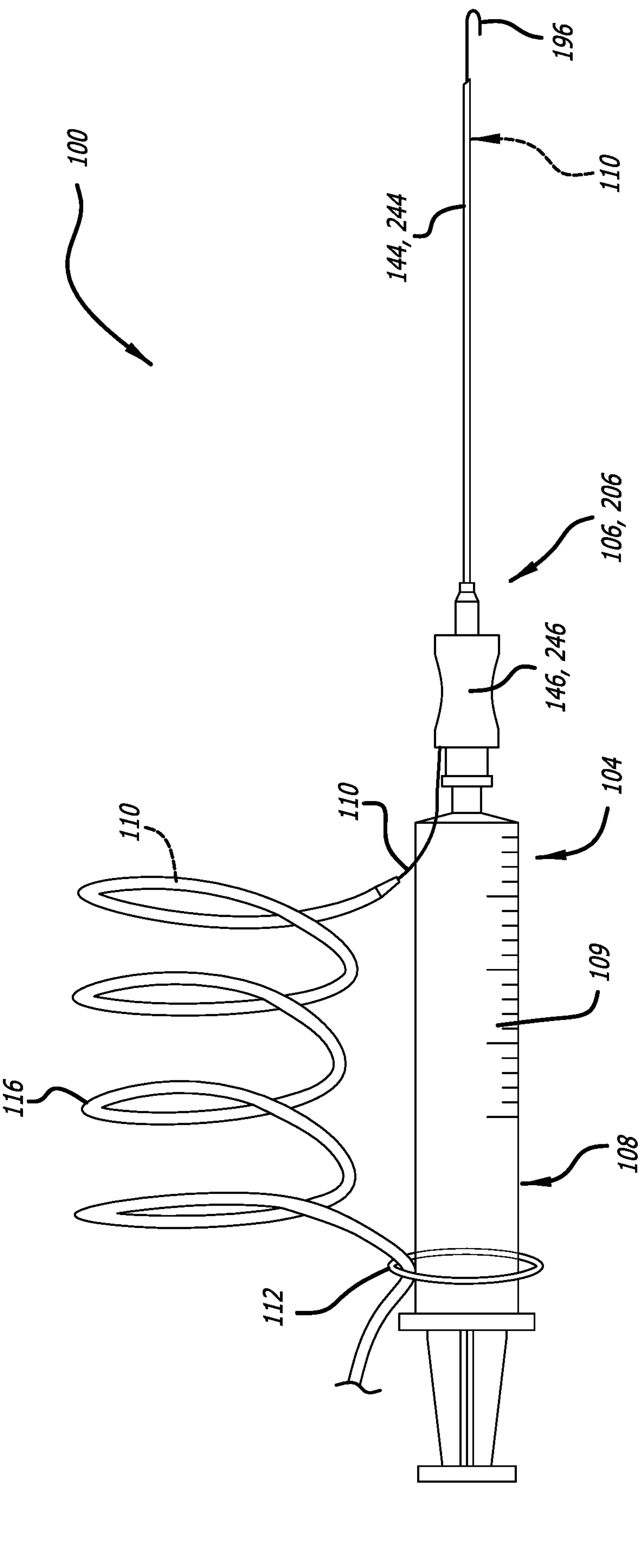
FIG. 16 illustrates the RICC insertion assembly with the seventh coupler coupling together the catheter tube of the RICC and the barrel of the syringe of the introducer assembly to enforce a number of loops in the catheter tube of a second configuration in accordance with some embodiments.
Figure 17:
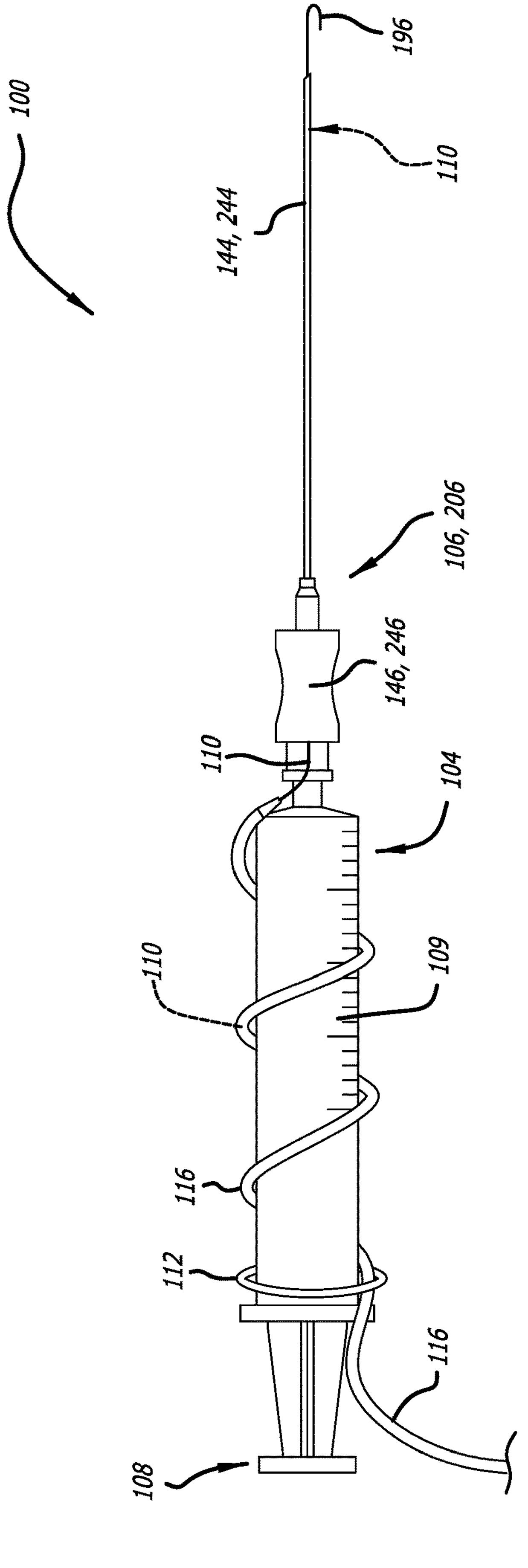
FIG. 17 illustrates the RICC insertion assembly with a number of loops in the catheter tube of a third configuration in accordance with some embodiments.
Figure 18:
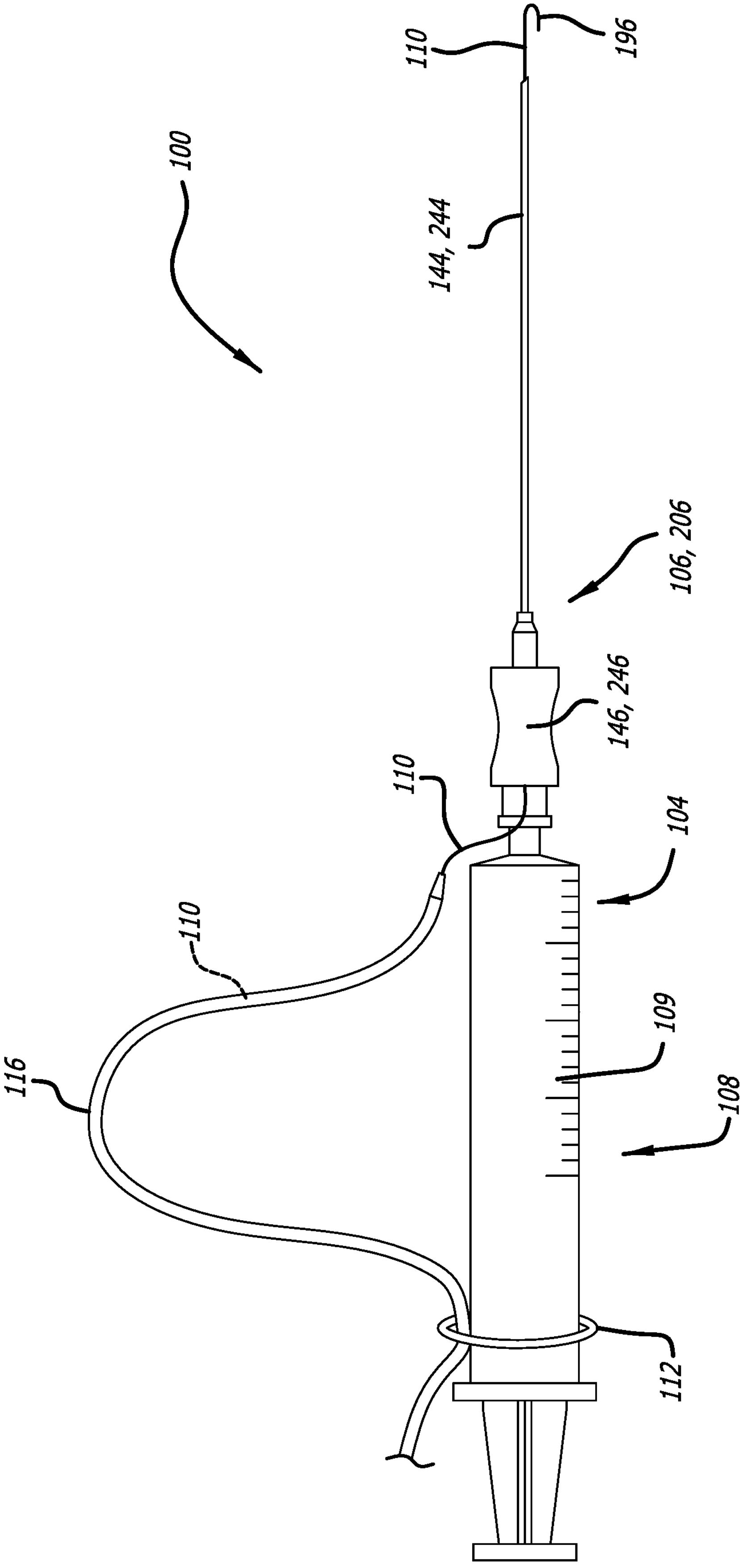
FIG. 18 illustrates the RICC insertion assembly with the seventh coupler coupling together the catheter tube of the RICC and the barrel of the syringe of the introducer assembly to enforce a protrusion in the catheter tube of a first configuration in accordance with some embodiments.
Figure 19:
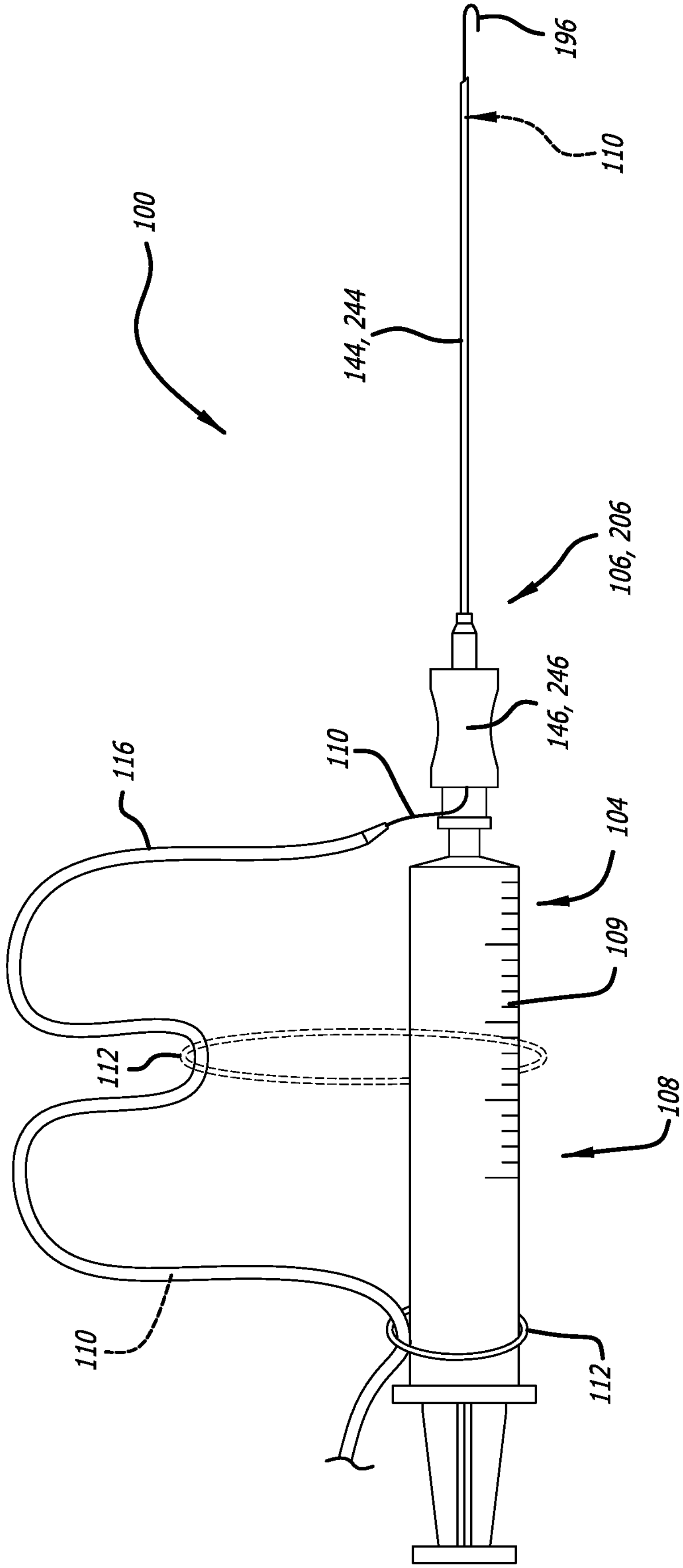
FIG. 19 illustrates the RICC insertion assembly with the seventh coupler coupling together the catheter tube of the RICC and the barrel of the syringe of the introducer assembly to enforce a protrusion in the catheter tube of a second configuration in accordance with some embodiments.

FIGS. 12 and 13 illustrate various view of the coupler 112 coupling together the RICC 102 and the access guidewire 110 in accordance with some embodiments.

As shown in FIG. 12, the coupler 112 coupling together the RICC 102 and the access guidewire 110 can be a separate coupler including an access-guidewire clip 192 and the catheter-hub seat 184 opposite the access-guidewire clip 192. Like that set forth above, the coupler 112 being a separate coupler enables the catheter hub 118 to be decoupled from the coupler 112, thereby making the suture wings 186 of the catheter hub 118 available for securing (via suturing) the catheter hub 118 to a patient upon placing the RICC 102 in the patient's vasculature. However, the coupler 112 need not be a separate coupler. As an alternative, the coupler 112 can be an integrated coupler. Indeed, the coupler 112 can be a portion of the catheter hub 118 such as an access-guidewire clip integrated into a patient-facing side of the catheter hub 118 or even an adhesive disposed on the patient-facing side of the catheter hub 118 configured to adhere the access guidewire 110 thereto. Advantageously, such an adhesive can further function to secure the catheter hub 118 to skin of the patient upon placing the RICC 102 in the patient's vasculature.

When the coupler 112 is a separate coupler, the access-guidewire clip 192 of the coupler 112 can be a Terry-type clip extending from the coupler 112 configured to slidably clip onto the access guidewire 110. When the coupler 112 is an integrated coupler, the access-guidewire clip of the coupler 112 can be a groove in the patient-facing side of the catheter hub 118 configured to slidably clip onto the access guidewire 110. Being that the outer diameter of the access guidewire 110 is relatively narrow (e.g., 0.035" or less), the groove in the catheter hub 118, too, can be relatively narrow. Such a relatively narrow groove in the catheter hub 118 minimally interferes with a surface of the patient-facing side of the catheter hub 118 keeping the catheter hub 118 available for securing the catheter hub 118 to a patient upon placing the RICC 102 in the patient's vasculature.

When the coupler 112 is a separate coupler, the catheter-hub seat 184 of the coupler 112 is configured to seat the catheter hub 118 thereon. Notably, the catheter-hub seat 184 can include the posts 188 extending therefrom like those shown in at least FIGS. 3-6 and 9. Again, such posts are configured to insert into the suture-wing holes 190 of the suture wings 186 extending from the catheter hub 118 to secure the catheter hub 118 on the catheter-hub seat 184.

As shown in FIG. 13, the coupler 112 coupling together the RICC 102 and the access guidewire 110 can be a separate coupler including a clip, a band, or a releasable tie around both the catheter tube 116 and the access guidewire 110. Advantageously, such a clip, band, or tie does not interfere with the catheter hub 118 in any way, thereby keeping the catheter hub 118 available for securing the catheter hub 118 to a patient upon placing the RICC 102 in the patient's vasculature.

Notably, portions of the RICC 102 other than the catheter hub 118 and the catheter tube 116 can be coupled to the access guidewire 110, optionally, in combination with the catheter hub 118 or the catheter tube 116, to further place the RICC insertion assembly 100 in a compact form. Indeed, any of a number of portions of the RICC 102 can be coupled to the access guidewire 110 to enforce the loop 114 in the access guidewire 110 over which the catheter tube 116 follows. By enforcing the loop 114 in the access guidewire 110 and the catheter tube 116, the coupler 112 compacts the RICC insertion assembly 100 making it easier to handle, thereby reducing the likelihood of touch contamination.

FIGS. 14-19 illustrate various view of the coupler 112 coupling together the introducer assembly 104 and the access guidewire 110 in accordance with some embodiments.

As shown, the coupler 112 coupling together the introducer assembly 104 and the access guidewire 110 can be a separate coupler including a clip, a band, or a releasable tie around at least the access guidewire 110 up to both the introducer assembly 104 (e.g., the barrel 109 of the syringe 108) and the access guidewire 110. As an alternative, the coupler 112 can be an integrated coupler. Indeed, when the coupler 112 is an integrated coupler, the coupler 112 can be a portion of the syringe 108 such as a clip integrated into a barrel flange in a proximal end of the barrel 109 of the syringe 108 or even an adhesive disposed on the barrel 109 of the syringe 108 configured to adhere the access guidewire 110 thereto. Advantageously, such a clip, band, tie, or adhesive does not interfere with the catheter hub 118 in any way, thereby keeping the catheter hub 118 available for securing the catheter hub 118 to a patient upon placing the RICC 102 in the patient's vasculature.

Notably, portions of the RICC 102 such as those set forth above can be coupled to the introducer assembly 104 or the access guidewire 110 in combination with the coupler 112 coupling together the introducer assembly 104 and the access guidewire 110 to further place the RICC insertion assembly 100 in a compact form. Indeed, any of a number of portions of the RICC 102 can be coupled to the introducer assembly 104 or the access guidewire 110 to enforce the loop 114 in the access guidewire 110 over which the catheter tube 116 follows. By enforcing the loop 114 in the access guidewire 110 and the catheter tube 116, the coupler 112 compacts the RICC insertion assembly 100 making it easier to handle, thereby reducing the likelihood of touch contamination.

It should be understood that, in addition to the orientation of the loop 114 such as that responsive to the orientation of the catheter hub 118 with respect to the central axis of the introducer assembly 104, the loop 114 in the access guidewire 110 and the catheter tube 116 thereover can have any of a number of topological configurations. Indeed, the loop 114 can be stretched out in any direction, compressed in any other direction, crossed over itself, or the like as long as there are no permanent deformations in the access guidewire 110 or the catheter tube 116. In addition, the loop 114 can have a handedness in that the loop 114 can be a left-handed loop or a right-handed loop in accordance with the so-called right-hand rule. For example, the loops shown FIGS. 1-4 and 9 are left-handed loops while the loops shown in FIGS. 5-8, 10, 11, 13, and 14 are right-handed loops. Lastly, it should be understood in view of at least FIGS. 15-19 that the access guidewire 110 and the catheter tube 116 thereover need not necessarily be enforced in the loop 114. Indeed, the access guidewire 110 and the catheter tube 116 thereover can instead be enforced in any of a number of geometric shapes including, but not limited to, multiple loops (see FIG. 15-17), optionally in a coil around the barrel 109 of the syringe 108 (see FIG. 17), a spiral, a 'U' shape or upside-down 'U' shape (see FIG. 18), a 'W' shape or an 'M' shape (see FIG. 19), or the like. Different geometric shapes having different orientations, topological configurations, handednesses, etc. provide clinicians different options in different procedural, environmental, or even personal circumstances to keep the RICC insertion assembly 100 in a compact form. Indeed, in a non-limiting example, a right-handed clinician might prefer the RICC insertion assembly 100 of FIGS. 1 and 2 with the left-handed loop 114 when performing the needle tract-establishing step set forth below. In contrast, a left-handed clinician might prefer the RICC insertion assembly 100 of FIGS. 5 and 6 with the right-handed loop 114.

FIGS. 30-33 illustrate the coupler 112 coupling together the introducer assembly 104 and the access guidewire 110 in accordance with some embodiments.

As shown, the coupler 112 can be an actuating coupler configured to couple together at least the introducer assembly 104 and the access guidewire 110. The coupler 112 can include a coupler housing 198 and a coupler-housing lock incorporated therein, which coupler-housing lock is discernable by the lever 204 of the coupler-housing lock shown in each figure of FIGS. 30-33. Notably, the coupler-housing lock can also be referred to as an access-guidewire clamp in that the access guidewire 110 can also be clamped by the coupler-housing lock in at least a ready-to-deploy state of the introducer assembly 104 as shown in FIGS. 30 and 32.

Figure 31:
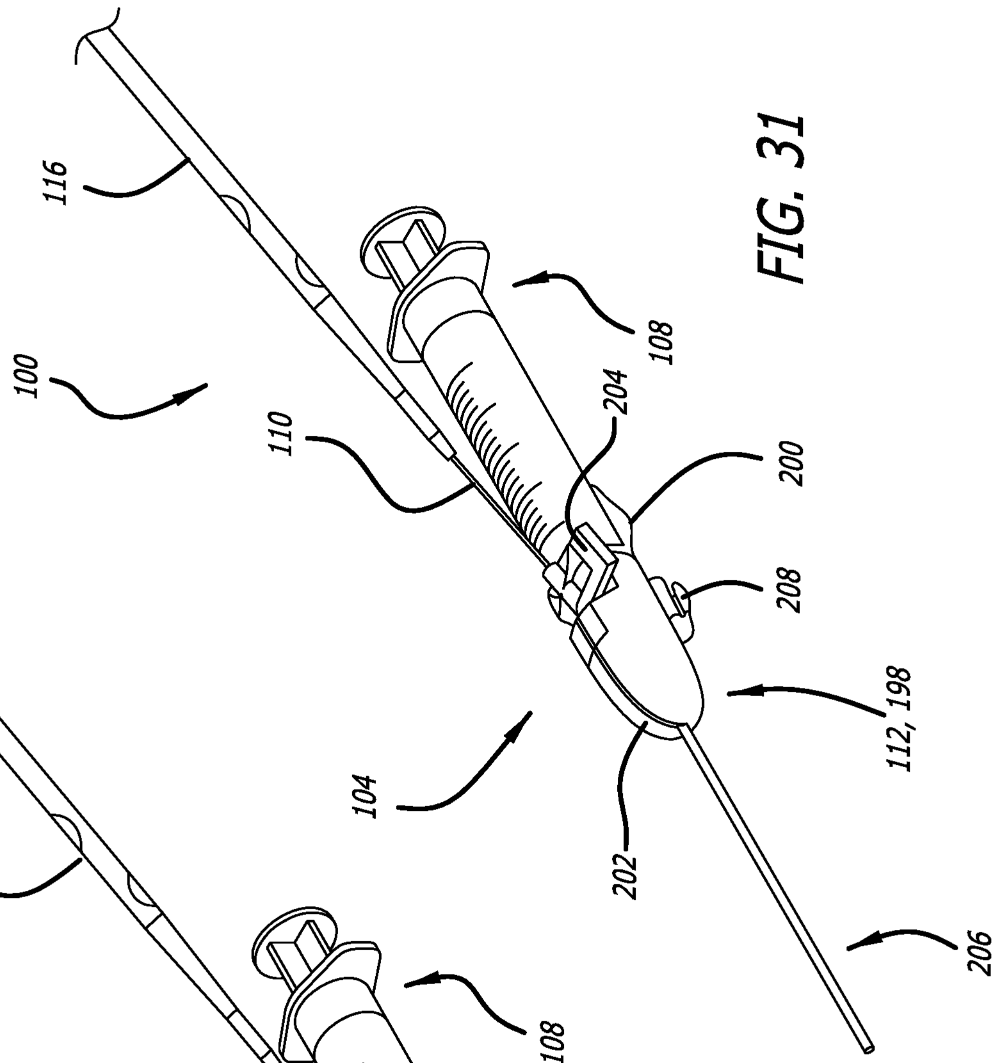
FIG. 31 illustrates the RICC insertion assembly with the actuating coupler coupling together the introducer assembly and the access guidewire in a second state of the actuating coupler in accordance with some embodiments.
Figure 30:
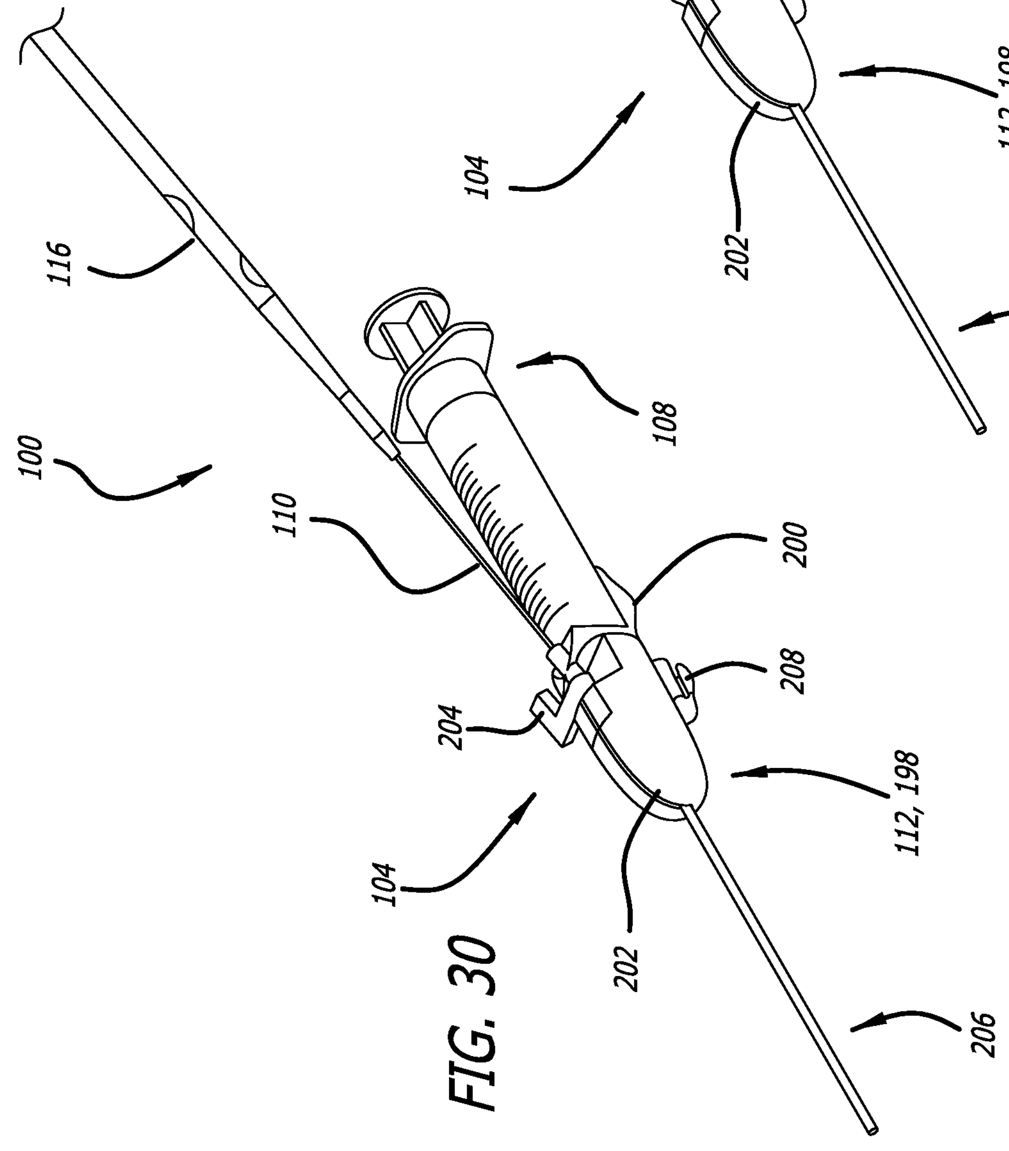
FIG. 30 illustrates the RICC insertion assembly with an eighth, actuating coupler coupling together the introducer assembly and the access guidewire in a first state of the actuating coupler in accordance with some embodiments.
Figure 32:
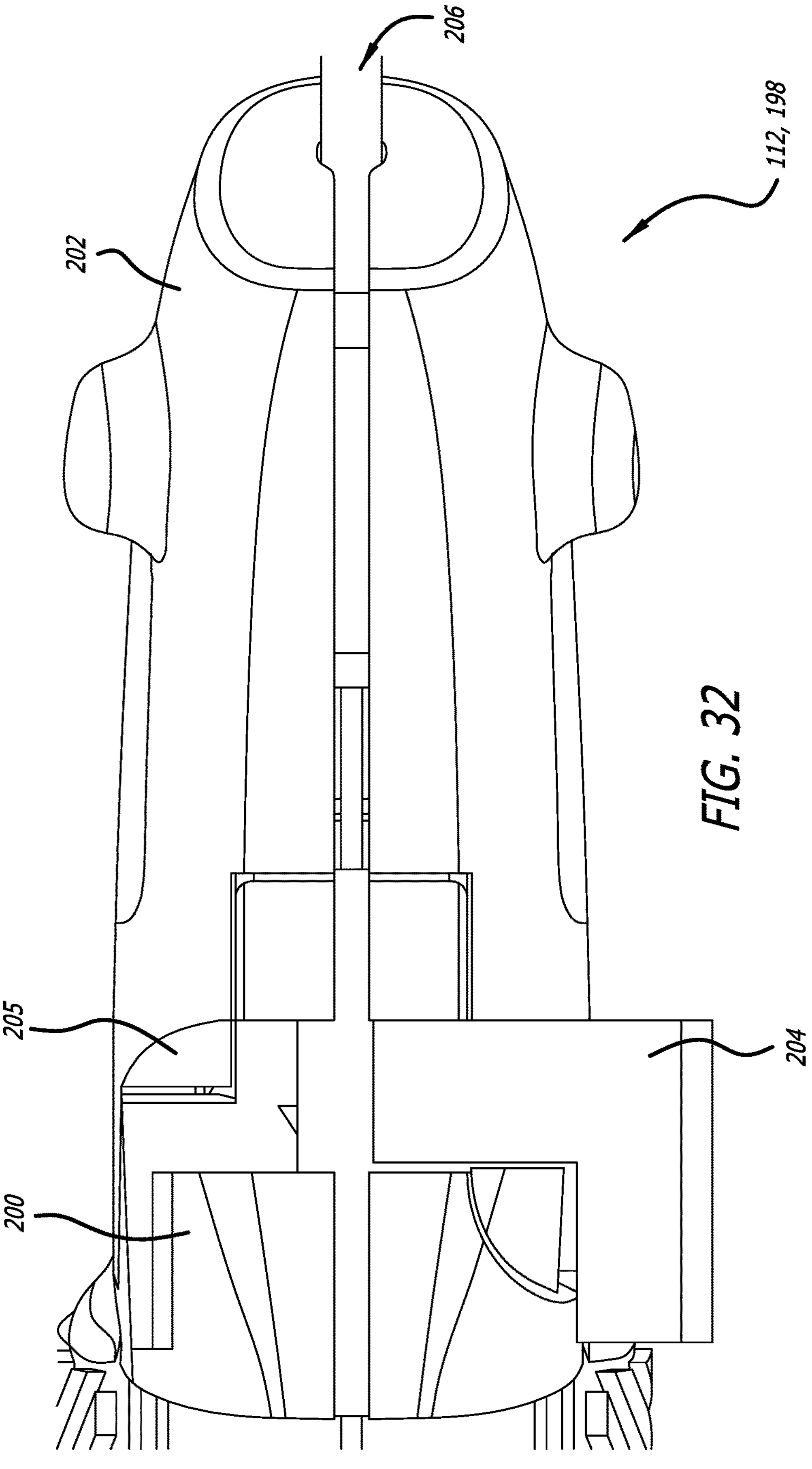
FIG. 32 illustrates a detailed view of the actuating coupler in the first state of the actuating coupler in accordance with some embodiments.

The coupler housing 198 can include a proximal coupler-housing piece 200 and a distal coupler-housing piece 202; however, the proximal coupler-housing piece 200 can also be referred to as a needle hub as the needle hub in the introducer assembly 104 best shown in FIGS. 30 and 31 doubles as the proximal coupler-housing piece 200. As further shown in FIGS. 30 and 32, the proximal coupler-housing piece 200 is nested in and locked to the distal coupler-housing piece 202 by way of the coupler-housing lock in at least the ready-to-deploy state of the introducer assembly 104. But the proximal coupler-housing piece 200 can still be nested in the distal coupler-housing piece 202 when the proximal coupler-housing piece 200 is unlocked from the distal coupler-housing piece 202 as shown in FIG. 31. That said, the coupler-housing lock can include the cam 205 set forth below for distally pushing the distal coupler-housing piece 202 away from the proximal coupler-housing piece 200 when the lever 204 of the coupler-housing lock is rotated from the first or locked state of the coupler-housing lock or coupler 112 shown in FIG. 32 into the second or unlocked state of the coupler-housing lock or coupler 112 shown in FIG. 33.

Each piece of the proximal and distal coupler-housing pieces 200 and 202 can include two molded pieces coupled together such as fastened or screwed together with screws or bolts, bonded together with an adhesive, or a combination thereof. An inside of each piece of the two molded pieces of the distal coupler-housing piece 202 can include a depression that forms a receptacle in a proximal portion of the distal coupler-housing piece 202 when the two molded pieces are coupled together. When the proximal and distal coupler-housing pieces 200 and 202 are nested together with a distal portion of the proximal coupler-housing piece 200 disposed in the receptacle of the distal coupler-housing piece 202 as shown in FIGS. 30-32, the proximal and distal coupler-housing pieces 200 and 202 form a bullet-shaped body. The bullet-shaped body of the coupler 112 is configured to be comfortably held underhand (e.g., cradled) in either a left hand for a left-handed venipuncture or a right hand for a right-handed venipuncture with the RICC insertion assembly 100. It should be understood, however, that the body of the coupler 112 is not limited to a bullet shape.

The coupler-housing lock can be incorporated in the coupler 112 with a rotatable lever 204 including an extension channel 179 configured to extend the access-guidewire channel 178 that directs the access guidewire 110 into the sheath opening 176 and the needle slot 166 of the introducer needle 206, albeit with the proximal coupler-housing piece 200 being the needle hub 246. (See, for example, FIG. 33, where the extension channel 179 extending the access-guidewire channel 178 through the lever 204 is an open channel in the second or unlocked state of the coupler-housing lock or coupler 112.) Alternatively, the coupler-housing lock can be incorporated in the coupler 112 with the lever 204 including the extension channel 179 configured to extend the needle-hub through hole 154 of the introducer needle 106, albeit with the proximal coupler-housing piece 200 being the needle hub 146. When the lever 204 of the coupler-housing lock is rotated into a first or locked state of the coupler-housing lock or coupler 112 as shown in FIGS. 30 and 32, a clamping portion of the lever 204 can clamp or otherwise hold the access guidewire 110 in place such as by rotation of the clamping portion of the lever 204 over the access guidewire 110. The clamping portion of the lever 204 can be the extension channel 179, itself, when inverted by rotation of the lever 204 to mate with an inboard mating piece or portion of the coupler housing 198 to clamp the access guidewire 110. Alternatively, the clamping portion of the lever 204 can be the extension channel 179, itself, when inverted by rotation of the lever 204 to misalign with the access-guidewire channel 178 or the needle-hub through hole 154, thereby creating a tortured path for holding the access guidewire 110. When the lever 204 of the coupler-housing lock is rotated from the first or locked state of the coupler-housing lock or coupler 112 into a second or unlocked state of the coupler-housing lock or coupler 112 as shown in FIGS. 31 and 33, the clamping portion of the lever 204 can release the access guidewire 110, thereby allowing the access guidewire 110 to be distally advanced into the coupler 112 or proximally withdrawn from the coupler 112.

Figure 33:
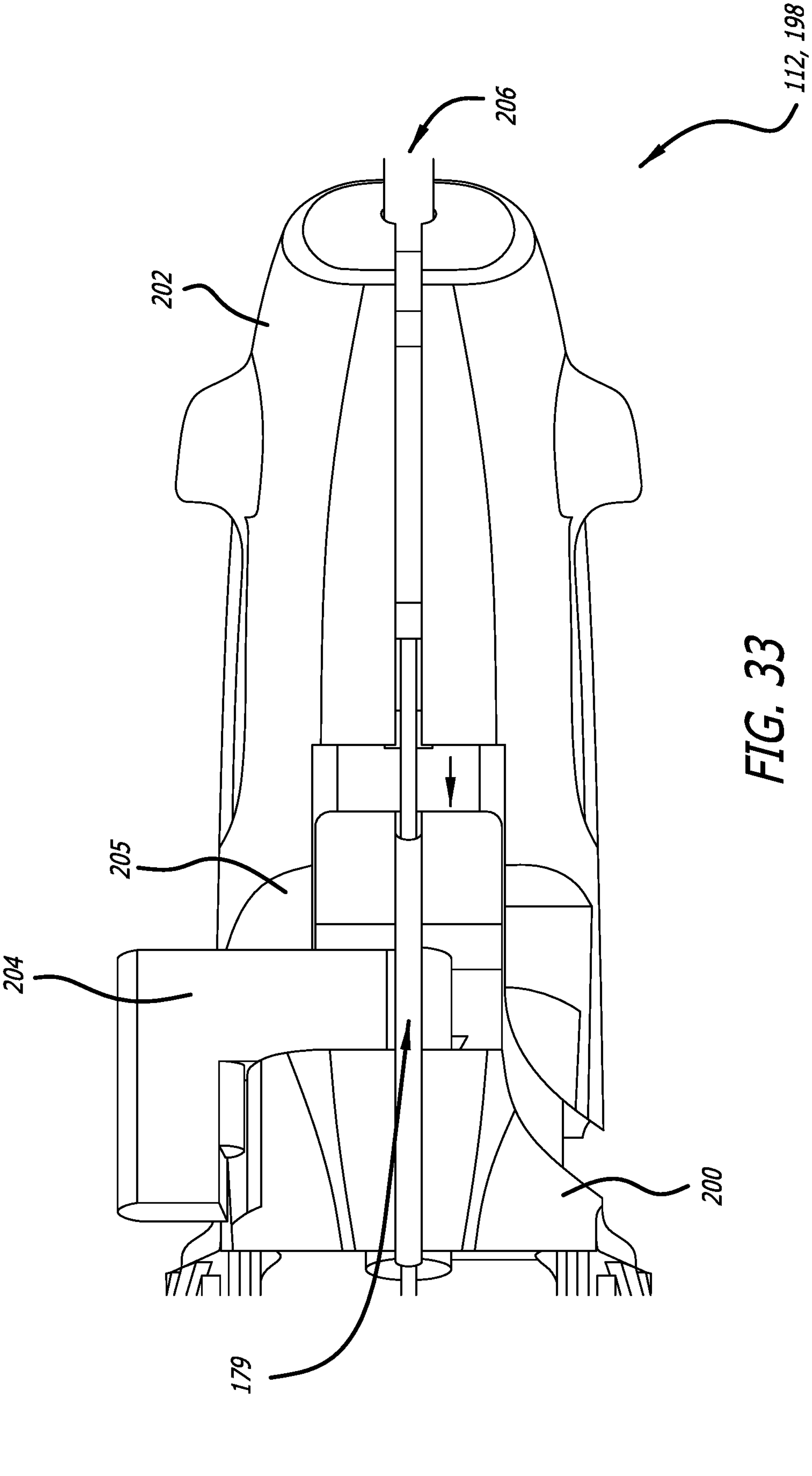
FIG. 33 illustrates a detailed view of the actuating coupler in the second state of the actuating coupler in accordance with some embodiments.

The coupler-housing lock can also include a cam 205 (e.g., a wedge cam) configured to cooperate with an edge of the lever 204 as a follower of the cam 205 and distally push the distal coupler-housing piece 202 away from the proximal coupler-housing piece 200 when the lever 204 of the coupler-housing lock is rotated from the first or locked state of the coupler-housing lock or coupler 112 shown in FIGS. 30 and 32 to the second or unlocked state of the coupler-housing lock or coupler 112 shown in FIGS. 31 and 33. As shown in the foregoing figures, the cam 205 can be an angled or scooped face of the distal coupler-housing piece 202 facing the lever 204, and the lever 204 can be held captive in the proximal coupler-housing piece 200 such that the distal coupler-housing piece 202 is distally pushed away from the proximal coupler-housing piece 200 as the lever 204 is rotated into and follows along the angled or scooped face of the distal coupler-housing piece 202 forming the cam 205. Notably, such a mechanical linkage of the cam 205 and the following lever 204 is not limited to the foregoing. Indeed, the mechanical linkage could instead be an inverse of the foregoing with the cam protruding from the lever 204 over which an edge of the distal coupler-housing piece 202 follows to distally push the distal coupler-housing piece 202 away from the proximal coupler-housing piece 200 when the lever 204 of the coupler-housing lock is rotated from the first or locked state of the coupler-housing lock or coupler 112 to the second or unlocked state of the coupler-housing lock or coupler 112.

The coupler housing 198 can also include a catheter clip 208 configured for suspending the RICC 102 thereby in at least the ready-to-deploy state of the RICC insertion assembly 100. For example, the catheter clip 208 can be configured to suspend the RICC 102 by the catheter hub 118 or the one-or-more extension legs 120 in the ready-to-deploy state of the RICC insertion assembly 100. With the proximal portion of the access guidewire 110 disposed in the RICC 102 and the distal portion of the access guidewire 110 disposed in the introducer needle 206 in at least the ready-to-deploy state of the RICC insertion assembly 100, a loop in the access guidewire 110 is enforced over which the RICC 102 is disposed, thereby providing the RICC insertion assembly 100 in a compact form.

The access guidewire 110 includes a proximal portion including a proximal end and a distal portion including a distal end. The proximal end of the access guidewire 110 is coupled to an access-guidewire hub 194, which, in turn, can be connected to an extension-leg connector of the one-or-more extension-leg connectors 122. In at least a ready-to-deploy state of the RICC insertion assembly 100, the proximal portion of the access guidewire 110 is disposed in and extends along the primary lumen 132 of the RICC 102. The distal portion of the access guidewire 110 is disposed in and extends along the needle-shaft lumen 150 by way of the needle-hub through hole 154. Alternatively, the distal portion of the access guidewire 110 is disposed in and extends along the needle lumen of the introducer needle 206. As shown in FIG. 21, the guidewire tip 196 including the distal end of the access guidewire 110 is disposed in the needle-shaft lumen 150 just proximal of the needle tip 148 of the introducer needle 106 in the ready-to-deploy state of the RICC insertion assembly 100. Notably, the access guidewire 110 is similarly disposed in the RICC insertion assembly 100 in which the introducer assembly 104 includes the introducer needle 206. Disposed as such in the RICC insertion assembly 100, the proximal and distal portions of the access guidewire 110 can enforce the loop 114 or another geometrical shape in the access guidewire 110 in the ready-to-deploy state of the RICC insertion assembly 100. Because the RICC 102 is disposed over the access guidewire 110, the RICC insertion assembly 100 can have a relatively compact form in the ready-to-deploy state thereof.

The access guidewire 110 can include a guidewire tip 196 in the distal portion of the access guidewire 110, which adopts a ‘J’ shape configured to prevent puncturing a back wall of a blood vessel. Such a guidewire tip assumes a straightened state in the ready-to-deploy state of the RICC insertion assembly 100 and a curved state (i.e., the ‘J’ shape) when the guidewire tip 196 is advanced beyond the needle tip 148 or 248 (e.g., advanced into a blood-vessel lumen) in a deployed state of the RICC insertion assembly 100.

The access guidewire 110 can further include a bare-wire portion and a wound-wire portion proximal of the bare-wire portion. While not shown, the wound-wire portion of the access guidewire 110, when present, proximally extends from the guidewire tip 196 to the bare-wire portion of the access guidewire 110. While not shown, the bare-wire portion of the access guidewire 110, when present, distally extends through the needle-hub through hole 154 or sheath opening 176 in at least the ready-to-deploy state of the RICC insertion assembly 100 such that the gasket 160 or 260 forms a fluid-tight seal around the bare-wire portion of the access guidewire 110. Notably, the foregoing bare-wire portion can instead be a flat-wound or ground-wound portion of the access guidewire 110, wherein the flat-wound portion includes windings of a tape instead of a round wire, and wherein the ground-wound portion includes windings of a round wire ground down to flatten the windings.

Optionally, any exposed portion of the access guidewire 110 in the ready-to-deploy state of the RICC insertion assembly 100 such as that between the catheter tip 130 and the needle-hub through hole 154 can be disposed in sterile packaging such as a sterile bag or tube. In this way, the access guidewire 110 can be free from touch contamination and remain sterile prior to use. Notably, the catheter tube 116 of the RICC 102, too, can be disposed in the sterile packaging, thereby keeping the catheter tube 116 free from touch contamination and sterile prior to use.

Methods

Methods include methods of using the RICC insertion assembly 100. For example, a method can include using the RICC insertion assembly 100 to secure access to a blood-vessel lumen of a patient, place the RICC 102 in blood-vessel lumen, or the like. Such a method can include one or more steps selected from an assembly-obtaining step, an assembly-adjusting step, a needle tract-establishing step, a blood-aspirating step, an access guidewire-advancing step, an introducer needle-withdrawing step, a catheter tube-advancing step, an access guidewire-withdrawing step, a maneuver guidewire-advancing step, an additional catheter tube-advancing step, and a maneuver guidewire-withdrawing step.

The assembly-obtaining step includes obtaining the RICC insertion assembly 100. As set forth above, the RICC insertion assembly 100 includes, in the ready-to-deploy state thereof, the RICC 102, the introducer assembly 104, the access guidewire 110, and the coupler 112 coupling together the RICC 102 and the introducer assembly 104. The introducer assembly 104 includes the syringe 108 coupled to the introducer needle 106 or 206. The introducer needle 106 or 206 includes the needle hub 146 or 246 over the proximal portion of the needle shaft 144 or 244. The access guidewire 110 includes the proximal portion disposed in the primary lumen 132 of the RICC 102. The access guidewire 110 also includes the distal portion disposed in the needle-shaft lumen 150 of the needle shaft 144 by way of the needle-hub through hole 154 passing through the side of the needle hub 146. Alternatively, the distal portion of the access guidewire 110 is disposed in the needle lumen of the introducer needle 206 by way of the sheath opening 176. The coupler 112, by coupling together the RICC 102 and the introducer assembly 104, enforces the loop 114 in the access guidewire 110 over which the catheter tube 116 follows. By enforcing the loop 114 in the access guidewire 110 and the catheter tube 116, the coupler 112 compacts the RICC insertion assembly 100 making it easier to handle, thereby reducing the likelihood of touch contamination.

The assembly-adjusting step includes adjusting the RICC insertion assembly 100 to be in the ready-to-deploy state thereof before the establishing of the needle tract if the RICC insertion assembly 100 is not already in the ready-to-deploy state upon the obtaining of the RICC insertion assembly 100 in the assembly-obtaining step. Notably, the assembly-adjusting step can include adjusting an orientation, a topological configuration, a handednesses, or the like of the loop 114 to accommodate procedural, environmental, or even personal circumstances for the loop 114 to make the RICC insertion assembly 100 easier to handle.

The needle tract-establishing step includes establishing a needle tract from an area of skin to a blood-vessel lumen of a patient with the introducer needle 106 or 206. The needle tract-establishing step includes ensuring blood flashes back into the needle hub 146 or 246 of the introducer needle 106 or 206, the syringe tip of the syringe 108, the barrel 109 of the syringe 108, or a combination thereof. The ensuring of the blood flashing back into the needle hub 146 or 246 of the introducer needle 106 or 206, the syringe tip of the syringe 108, the barrel 109 of the syringe 108, or the combination thereof confirms the needle tract extends into the blood-vessel lumen. Notably, the needle tract-establishing step can include drawing a slight vacuum with the syringe 108 while establishing the needle tract for the ensuring of the blood flashing back into the needle hub 146 or 246 of the introducer needle 106 or 206, the syringe tip of the syringe 108, the barrel 109 of the syringe 108, or the combination thereof.

The blood-aspirating step includes aspirating blood with the syringe 108 for confirmation the needle tract extends into the blood-vessel lumen. The needle-hub through hole 154 includes the gasket 160 disposed therein forming the seal around the access guidewire 110. Likewise, the sheath opening 176 includes the gasket 260 dispose therein forming the seal around the access guidewire 110. The seal allows a vacuum to be drawn with the syringe 108 for the aspirating of the blood with the syringe 108 during the blood-aspirating step. In addition, the sheath 164 over the needle shaft 244 seals the needle slot 166 of the needle shaft 244 thereunder further allowing the vacuum to be drawn with the syringe 108 to aspirating of the blood with the syringe 108 during the blood-aspirating step.

The access guidewire-advancing step includes advancing the distal end of the access guidewire 110 into the blood-vessel lumen from its initial location in the needle shaft 144 or 244 just proximal of the needle tip 148 or 248 of the needle shaft 144 or 244. The access guidewire-advancing step secures access to the blood-vessel lumen with the access guidewire 110. Notably, the advancing of the distal end of the access guidewire 110 into the blood-vessel lumen simultaneously reduces a size of the loop 114 with the advancing of the access guidewire 110 during the access guidewire-advancing step.

The introducer needle-withdrawing step includes withdrawing the introducer needle 106 or 206 from the patient leaving the access guidewire 110 in place in the blood-vessel lumen. For example, the introducer needle-withdrawing step can include cutting the sheath 164 along the needle slot 166 and off the needle shaft 244 with a blade of choice (e.g., a scalpel blade) at some time before the introducer needle 206 is withdrawn from the patient or while performing the introducer needle-withdrawing step. The cutting of the sheath 164 off the needle shaft 244 allows the access guidewire 110 to escape from the needle shaft 244 by way of the needle slot 166. Again, the introducer needle 206 includes the needle slot 166 extending from the proximal portion of the needle shaft 244 through the needle tip 248, which allows the access guidewire 110 to escape from the introducer needle 206 with the cutting of the sheath 164 off the needle shaft 244.

The catheter tube-advancing step includes advancing the catheter tube 116 of the RICC 102 over the access guidewire 110 and into the blood-vessel lumen. The catheter tube-advancing step places the RICC 102 in the blood-vessel lumen in at least an initial placement.

The access guidewire-withdrawing step includes withdrawing the access guidewire 110 from the primary lumen 132 of the RICC 102, optionally, by way of the access-guidewire hub 194, leaving the catheter tube 116 in place in the blood-vessel lumen.

The maneuver guidewire-advancing step includes advancing a maneuver guidewire into the blood-vessel lumen by way of the primary lumen 132 of the RICC 102.

The additional catheter tube-advancing step includes advancing the distal portion of the catheter tube 116 of the RICC 102 farther into the blood-vessel lumen over the maneuver guidewire to a lower ⅓ of an SVC of a heart of the patient.

The maneuver guidewire-withdrawing step includes withdrawing the maneuver guidewire leaving the catheter tube 116 in place in the lower ⅓ of the SVC.

While the foregoing method is directed to use of the RICC insertion assemblies of FIGS. 1-11, the method can be modified for any RICC insertion assembly 100 of the RICC insertion assemblies of FIGS. 12-19, in which the coupler 112 couples together the RICC 102 and the access guidewire 110 or the introducer assembly 104 and the access guidewire 110.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central catheter ("RICC") insertion assembly, comprising:
- a RICC including:
  - a catheter tube;
  - a catheter hub coupled to a proximal portion of the catheter tube; and
  - one or more extension legs, each extension leg of the one or more extension legs having a distal portion coupled to the catheter hub;
- an introducer assembly including:
  - a syringe; and
  - an introducer needle coupled to the syringe, the introducer needle including:
    - a needle shaft; and
    - a needle hub over a proximal portion of the needle shaft, the needle hub including a needle-hub through hole passing through a side of the needle hub and connecting to a needle-shaft lumen;
- an access guidewire including:
  - a proximal portion disposed in a primary lumen of the RICC; and
  - a distal portion disposed in the needle-shaft lumen by way of the needle-hub through hole; and
- a coupler coupling together the introducer assembly and the access guidewire,
- wherein the coupler includes a rotatable lever of a coupler-housing lock of a coupler housing of the coupler, the coupler-housing lock having a locked state and an unlocked state respectively for locking and unlocking the needle hub from a distal coupler-housing piece of the coupler housing.

2. The RICC insertion assembly according to claim 1,
- wherein the locked state and the unlocked state of the coupler-housing lock are further respectively for clamping and unclamping the access guidewire.

3. The RICC insertion assembly according to claim 1, wherein the needle-hub through hole includes a gasket disposed therein configured to seal around the access guidewire and allow a vacuum to be drawn with the syringe without leaking through the needle-hub through hole.

4. The RICC insertion assembly according to claim 3, wherein the gasket includes one or more 'O'-rings.

5. The RICC insertion assembly according to claim 1, wherein
- the RICC includes a set of three lumens including the primary lumen, a secondary lumen, and a tertiary lumen.

6. The RICC insertion assembly according to claim 5, wherein the primary lumen has a primary-lumen aperture in a distal end of the catheter tube, the secondary lumen has a secondary-lumen aperture in a side of a distal portion of the catheter tube, and the tertiary lumen has a tertiary-lumen aperture in the side of the distal portion of the catheter tube proximal of the secondary-lumen aperture.

7. The RICC insertion assembly according to claim 1, wherein the RICC insertion assembly is in a ready-to-deploy state thereof with a guidewire tip of the access guidewire disposed just proximal of a needle tip of the introducer needle.

8. The RICC insertion assembly according to claim 7, wherein the guidewire tip is straight in the needle-shaft lumen in the ready-to-deploy state of the RICC insertion assembly but adopts a 'J' shape when advanced beyond the needle tip in a deployed state of the RICC insertion assembly.

9. The RICC insertion assembly according to claim 1, wherein the coupler housing includes a proximal coupler-housing piece nested in and locked to the distal coupler-housing piece by way of the coupler-housing lock in at least a ready-to-deploy state of the RICC insertion assembly.

10. The RICC insertion assembly according to claim 9, wherein the coupler-housing lock includes a cam configured to distally push the distal coupler-housing piece away from the proximal coupler-housing piece when the rotatable lever of the coupler-housing lock is rotated from the locked state to the unlocked state of the coupler-housing lock.

11. The RICC insertion assembly according to claim 10, wherein the cam is a wedge cam configured to cooperate with an edge of the rotatable lever as a follower of the cam.

12. The RICC insertion assembly according to claim 1, wherein the coupler housing includes a catheter clip configured for suspending the RICC in at least a ready-to-deploy state of the RICC insertion assembly.

13. The RICC insertion assembly according to claim 12, wherein the catheter clip is configured to suspend the RICC by the catheter hub or the one or more extension legs, thereby enforcing a loop in the access guidewire from the proximal portion of the access guidewire disposed in the primary lumen of the RICC to the distal portion of the access guidewire disposed in the needle-shaft lumen of the introducer needle.

* * * * *